US009566065B2

(12) United States Patent
Knodel

(10) Patent No.: US 9,566,065 B2
(45) Date of Patent: Feb. 14, 2017

(54) APPARATUS AND METHODS FOR SURGICAL STAPLER CLAMPING AND DEPLOYMENT

(71) Applicant: Cardica, Inc., Redwood City, CA (US)

(72) Inventor: Bryan D. Knodel, Flagstaff, AZ (US)

(73) Assignee: CARDICA, INC., Redwood City, CA (US)

( * ) Notice: Subject to any disclaimer, the term of this patent is extended or adjusted under 35 U.S.C. 154(b) by 477 days.

(21) Appl. No.: 14/135,368

(22) Filed: Dec. 19, 2013

(65) Prior Publication Data

US 2014/0175146 A1  Jun. 26, 2014

Related U.S. Application Data

(60) Provisional application No. 61/745,426, filed on Dec. 21, 2012.

(51) Int. Cl.
*A61B 17/04* (2006.01)
*A61B 17/10* (2006.01)
(Continued)

(52) U.S. Cl.
CPC ....... *A61B 17/068* (2013.01); *A61B 17/07207* (2013.01); *A61B 2017/0046* (2013.01);
(Continued)

(58) Field of Classification Search
CPC ........... A61B 2017/00477; A61B 2017/07214; A61B 2017/2943; A61B 2017/2923; A61B 2017/00323; A61B 17/00234; A61B 2017/00407
(Continued)

(56) References Cited

U.S. PATENT DOCUMENTS 4,354,628 A * 10/1982 Green ................. A61B 17/072
227/152
5,345,949 A * 9/1994 Shlain ................ A61B 17/0682
128/898
(Continued)

FOREIGN PATENT DOCUMENTS

EP   2044888   4/2009
EP   2140817   1/2010
(Continued)

OTHER PUBLICATIONS

Notification of Transmittal of the International Search Report and the Written Opinion of the International Searching Authority, PCT/US2013/077098, mailed Apr. 3, 2014.

*Primary Examiner* — Robert Long
(74) *Attorney, Agent, or Firm* — Vista IP Law Group, LLP

(57) ABSTRACT

A surgical stapling apparatus configured to perform stapling and/or cutting operations on a target tissue of a patient. The surgical stapling apparatus comprises of a mode selection switch to place the apparatus in either a clamping operational phase or a deployment operational phase. In the clamping operational phase, various clamp components are operated to facilitate loading of surgical staples into the stapling apparatus, if not preloaded, placement of the stapling apparatus to a target surgical site, and clamping of target tissue to be stapled and/or cut. In the deployment operational phase, various deployment components are operated to staple and/or cut the target tissue to one or more desired distance intervals to achieve the desired outcome for the surgical procedure.

11 Claims, 24 Drawing Sheets

(51) Int. Cl.
*A61B 17/068* (2006.01)
*A61B 17/072* (2006.01)
*A61B 17/29* (2006.01)
*A61B 17/00* (2006.01)

(52) U.S. Cl.
CPC ........... *A61B 2017/00393* (2013.01); *A61B 2017/00407* (2013.01); *A61B 2017/2923* (2013.01)

(58) Field of Classification Search
USPC .......................................... 227/175.1–182.1
See application file for complete search history.

(56) References Cited

U.S. PATENT DOCUMENTS

| | | | |
|---|---|---|---|
| 5,820,009 A | 10/1998 | Melling et al. | |
| 7,384,421 B2* | 6/2008 | Hushka | A61B 18/1445 606/41 |
| 7,588,175 B2 | 9/2009 | Timm et al. | |
| 7,819,296 B2 | 10/2010 | Huell et al. | |
| 7,832,408 B2* | 11/2010 | Shelton, IV | A61B 17/072 128/898 |
| 8,424,736 B2 | 4/2013 | Scirica et al. | |
| 8,602,288 B2 | 12/2013 | Shelton, IV et al. | |
| 2008/0046122 A1* | 2/2008 | Manzo | A61B 1/00149 700/245 |
| 2008/0308606 A1* | 12/2008 | Timm | A61B 17/07207 227/175.2 |
| 2008/0308607 A1* | 12/2008 | Timm | A61B 17/07207 227/176.1 |
| 2008/0314958 A1* | 12/2008 | Scirica | A61B 17/07207 227/175.2 |
| 2009/0145947 A1* | 6/2009 | Scirica | A61B 17/07207 227/175.2 |
| 2010/0170931 A1* | 7/2010 | Viola | A61B 17/128 227/175.1 |
| 2011/0295270 A1* | 12/2011 | Giordano | A61B 17/00234 606/130 |
| 2011/0295295 A1* | 12/2011 | Shelton, IV | A61B 17/072 606/170 |
| 2012/0138660 A1* | 6/2012 | Shelton, IV | B25C 5/0292 227/176.1 |
| 2012/0199630 A1* | 8/2012 | Shelton, IV | A61B 17/072 227/176.1 |
| 2012/0292367 A1* | 11/2012 | Morgan | A61B 17/072 227/175.1 |
| 2014/0332578 A1* | 11/2014 | Fernandez | A61B 17/068 227/175.1 |
| 2014/0339286 A1* | 11/2014 | Motooka | A61B 17/07207 227/175.2 |

FOREIGN PATENT DOCUMENTS

| | | |
|---|---|---|
| EP | 2286737 | 2/2011 |
| JP | 2009172386 | 8/2009 |
| WO | WO 2014011257 | 1/2014 |

\* cited by examiner

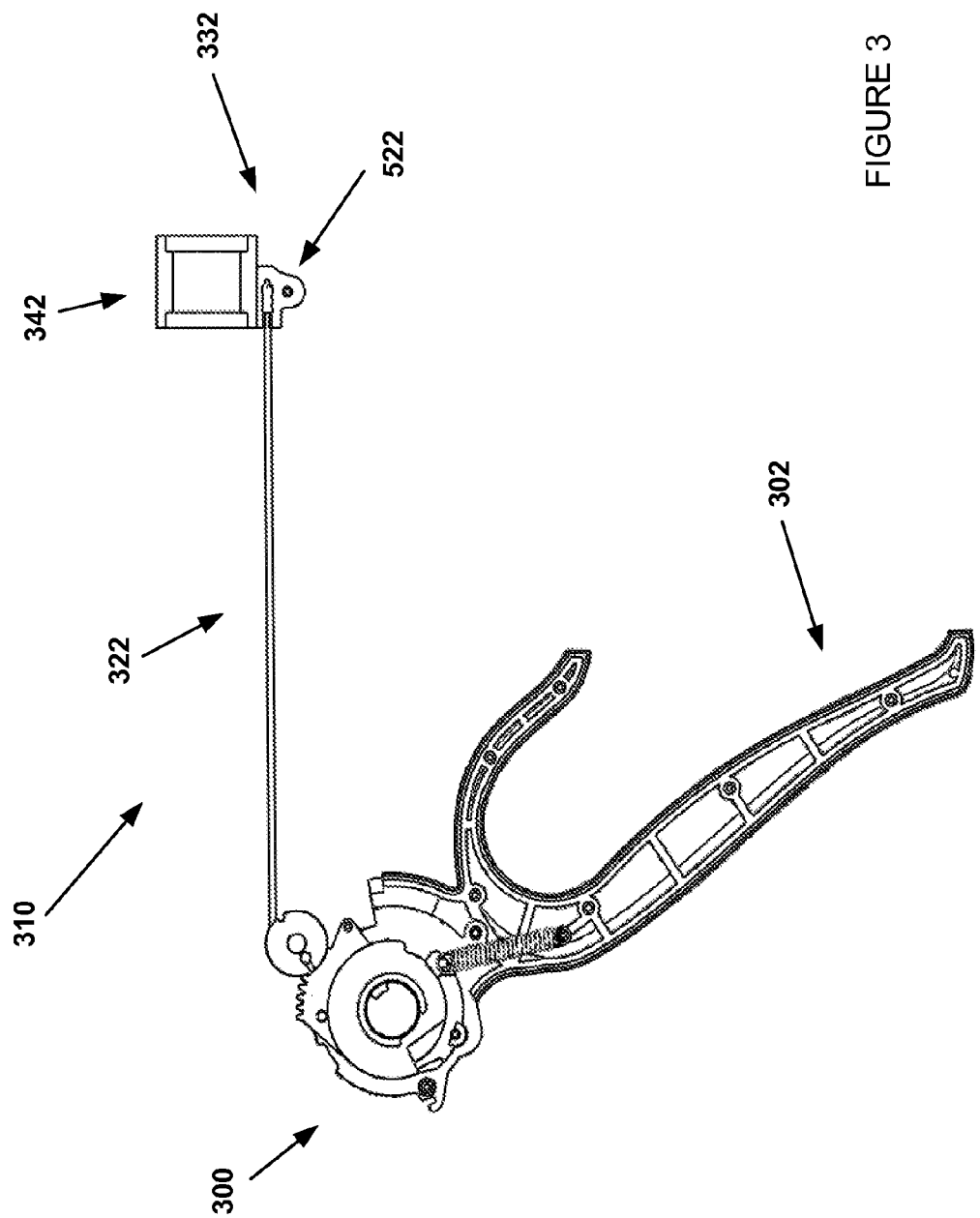

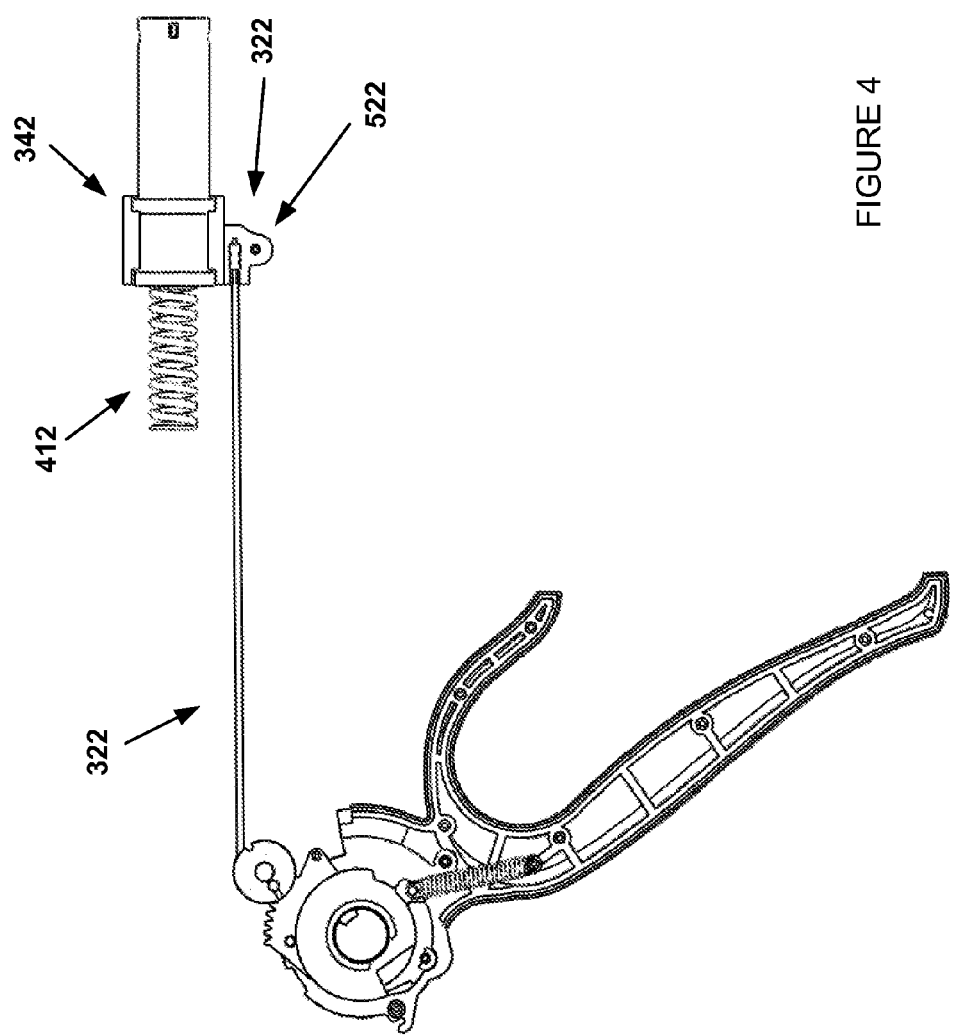

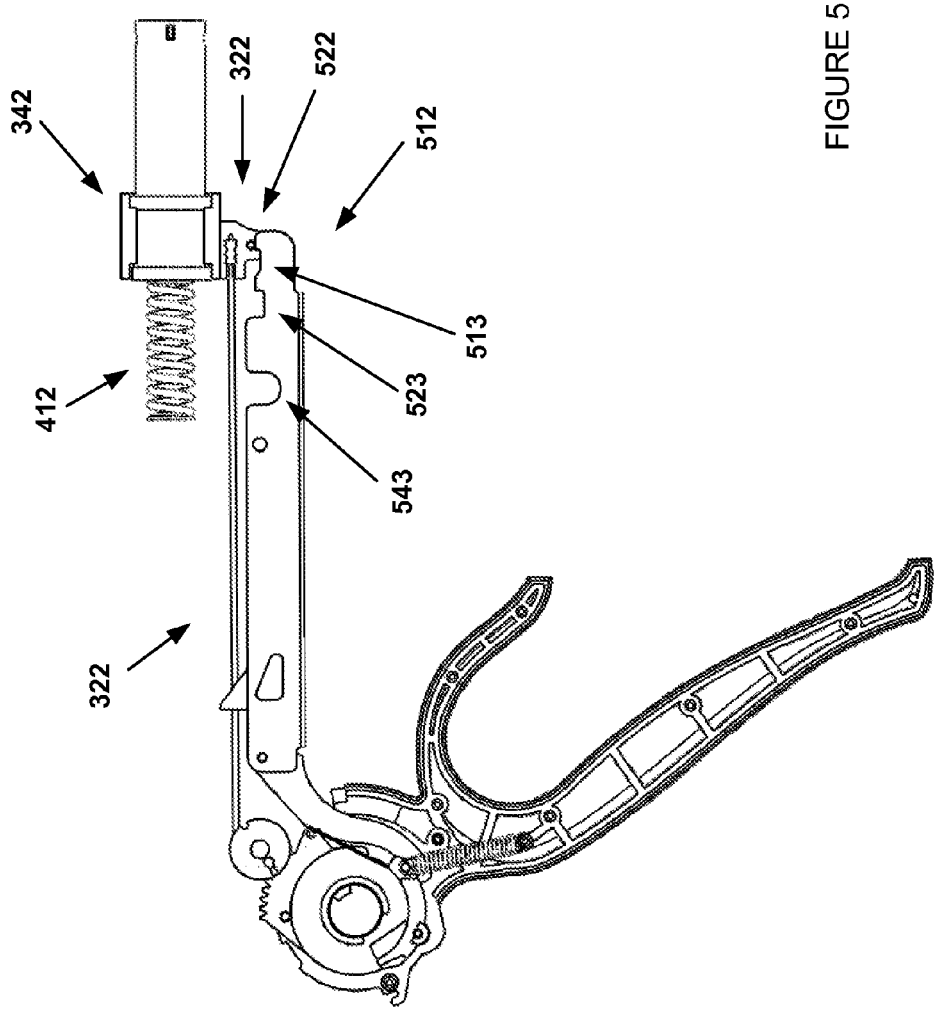

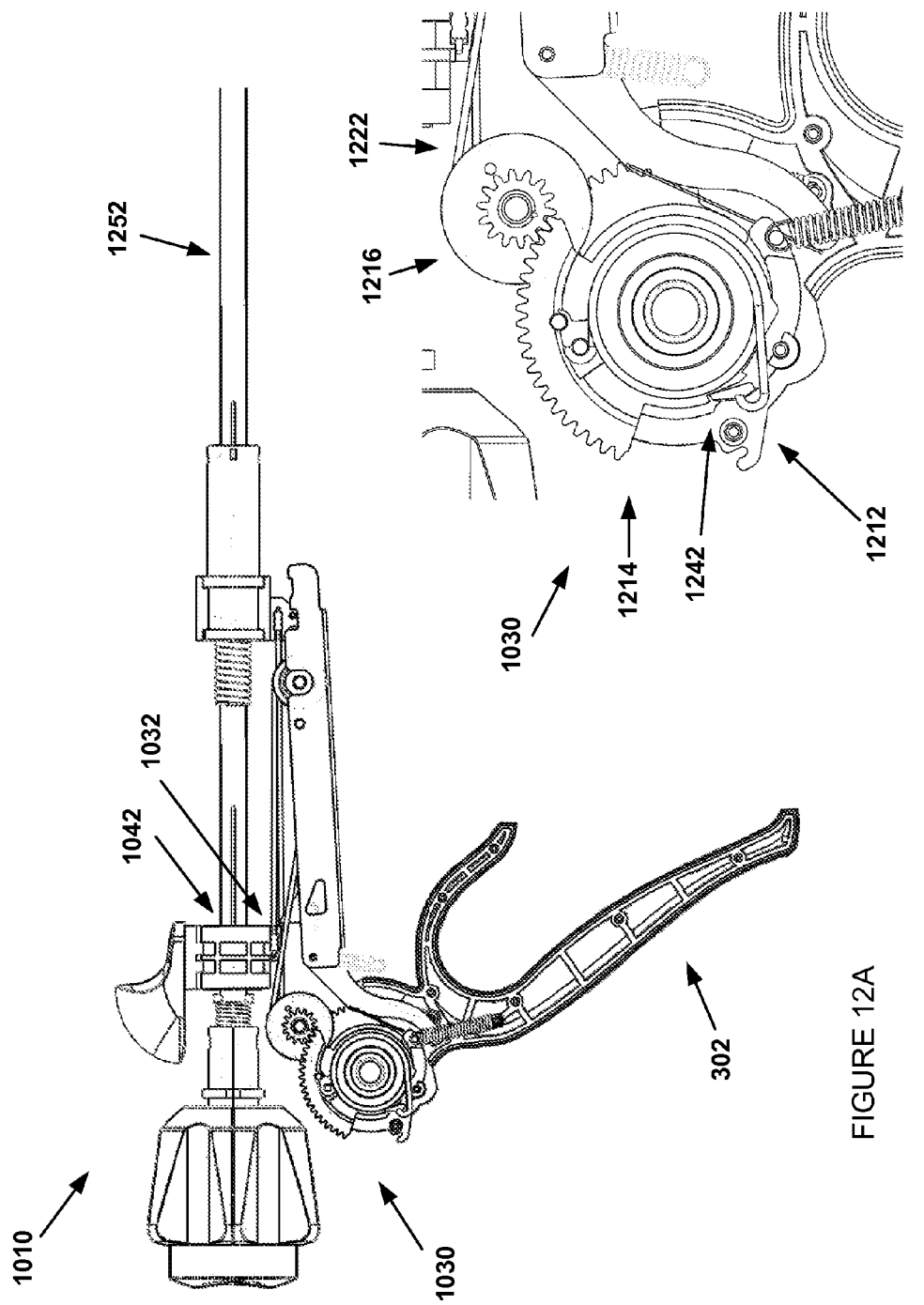

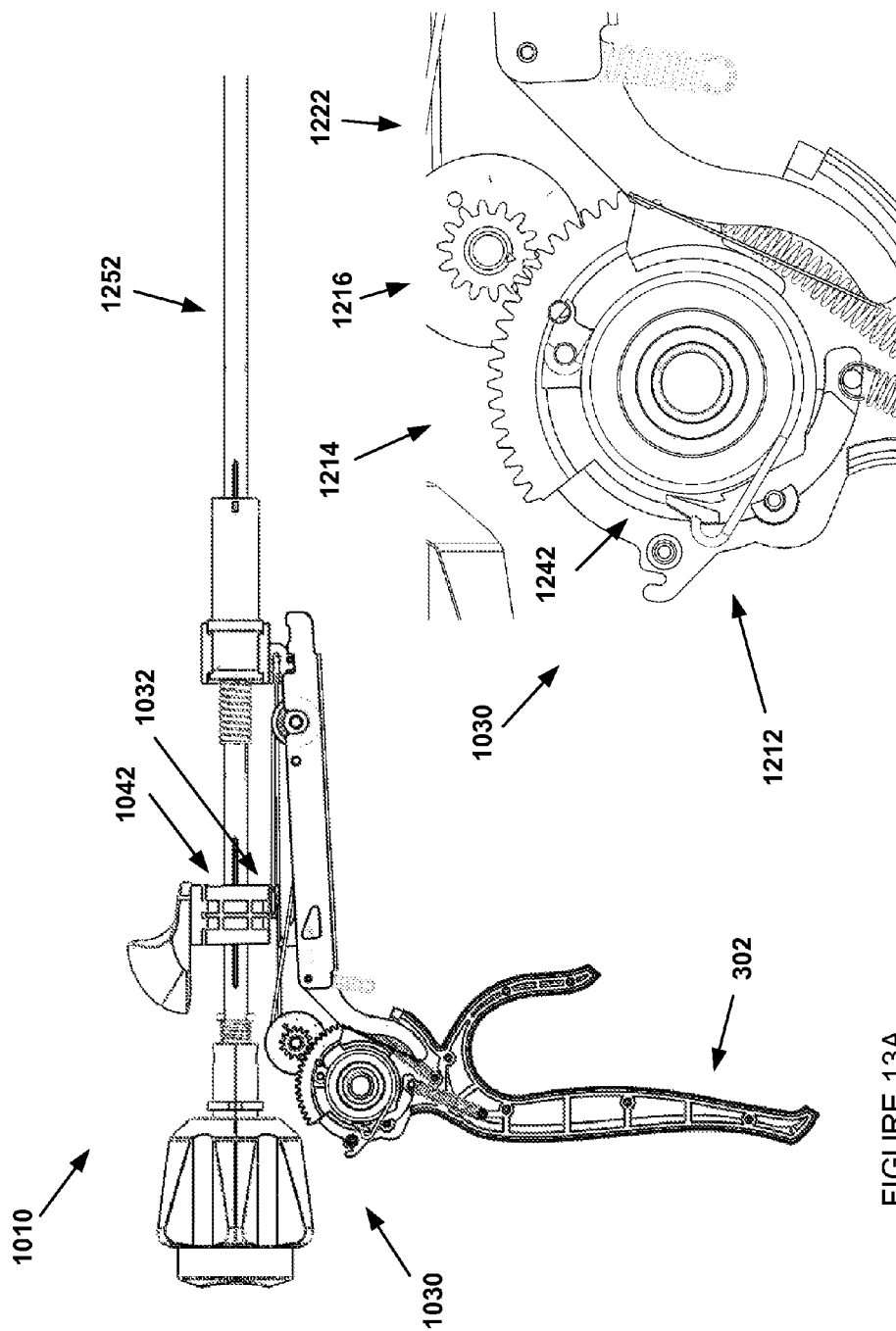

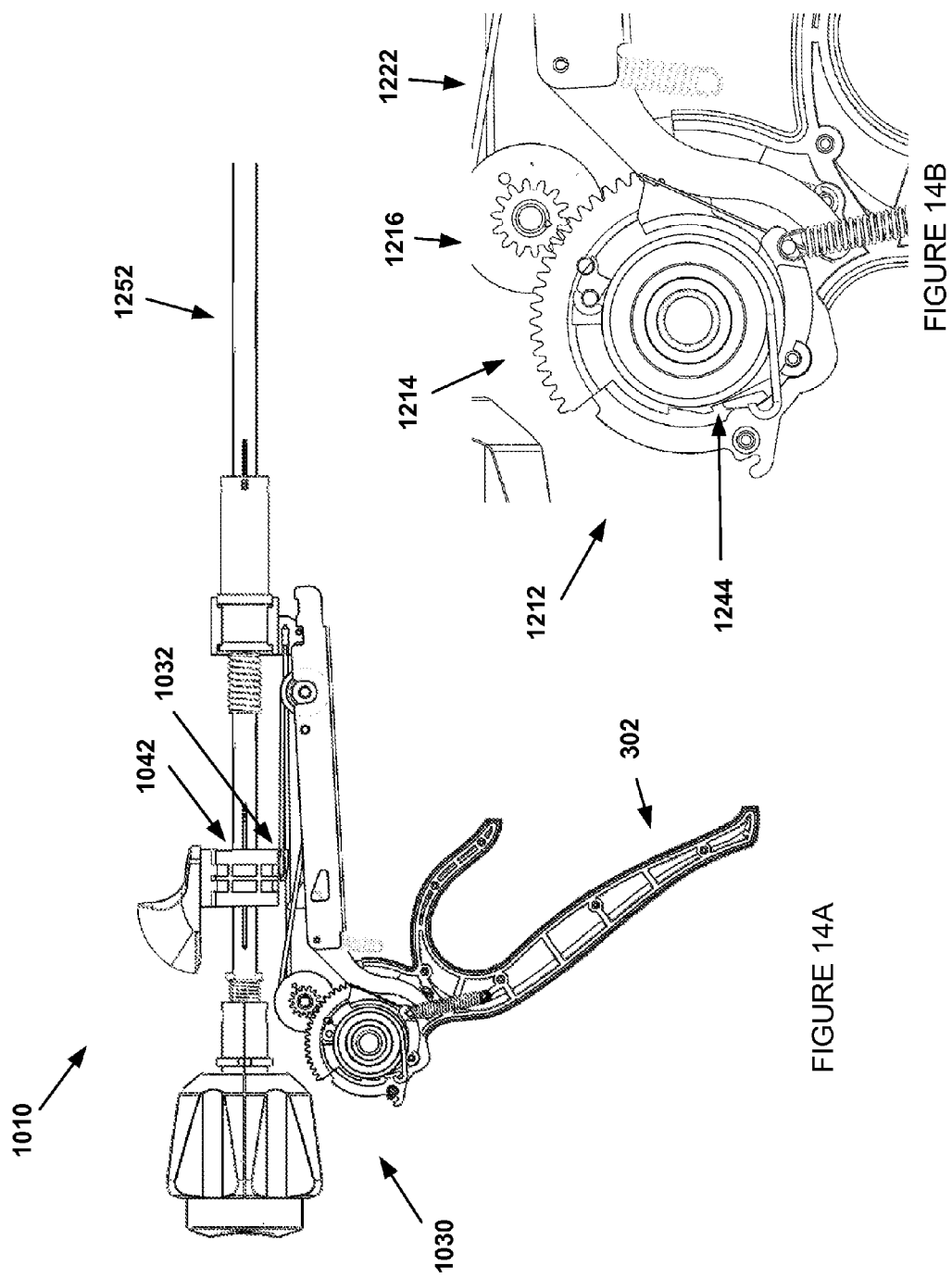

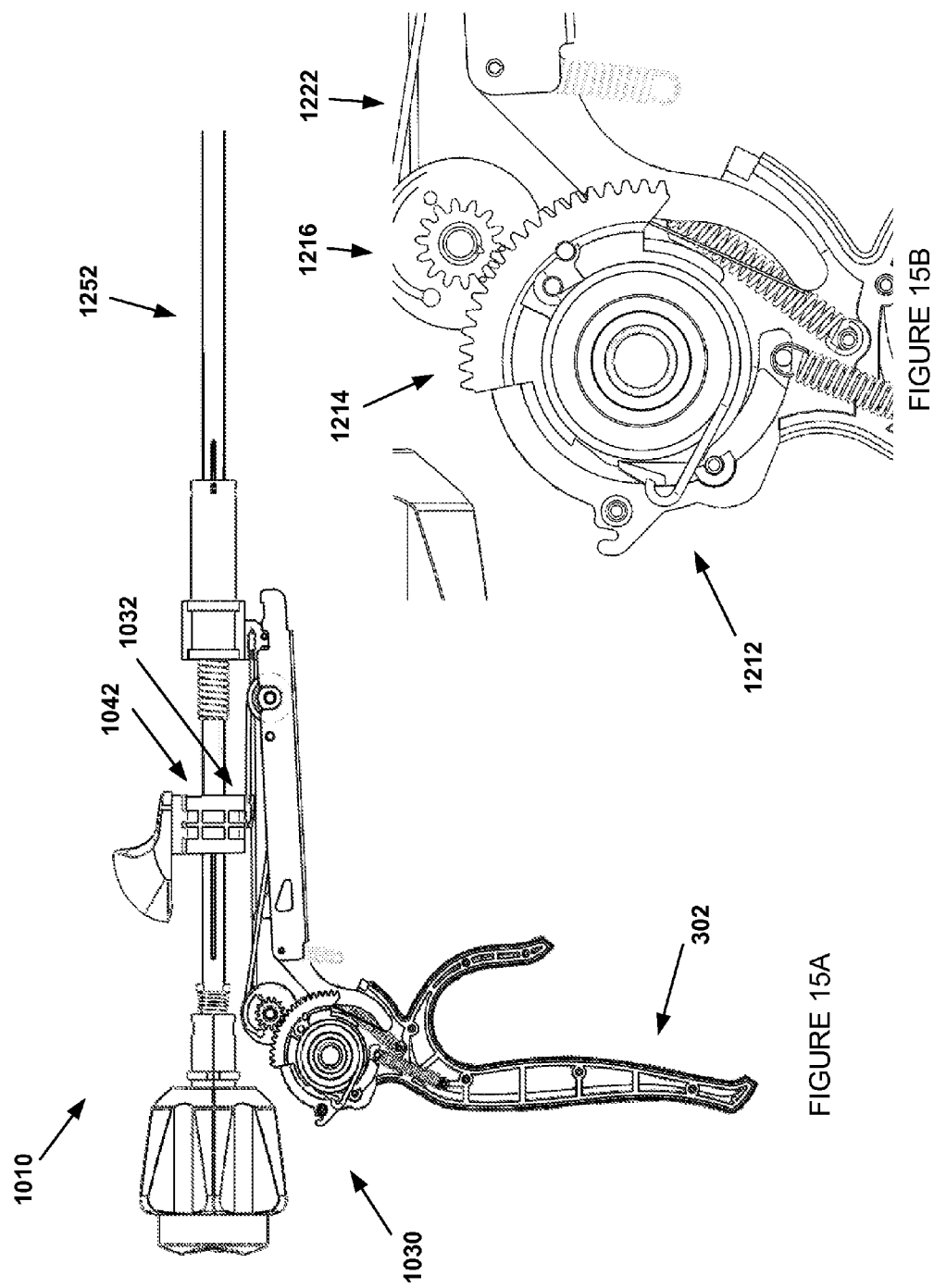

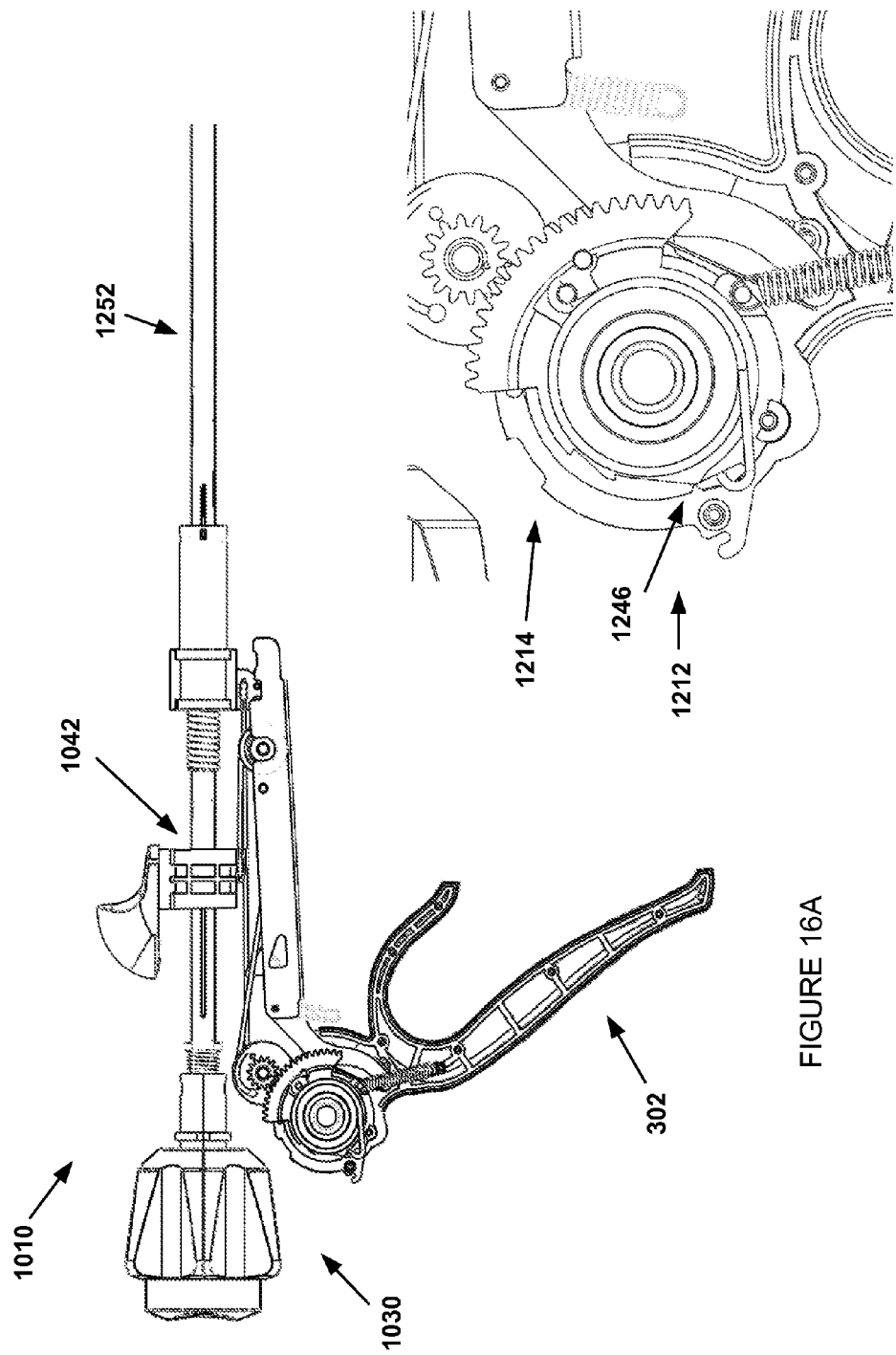

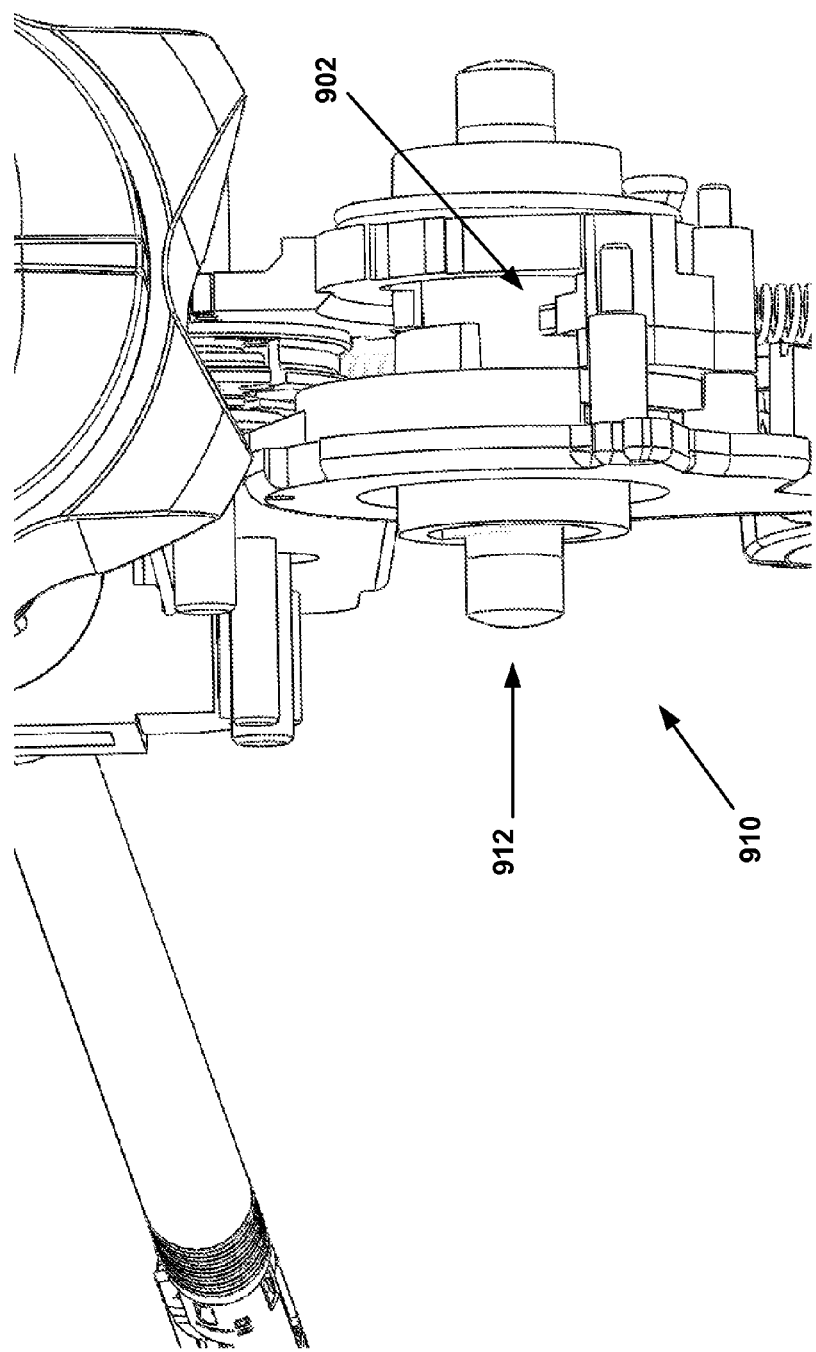

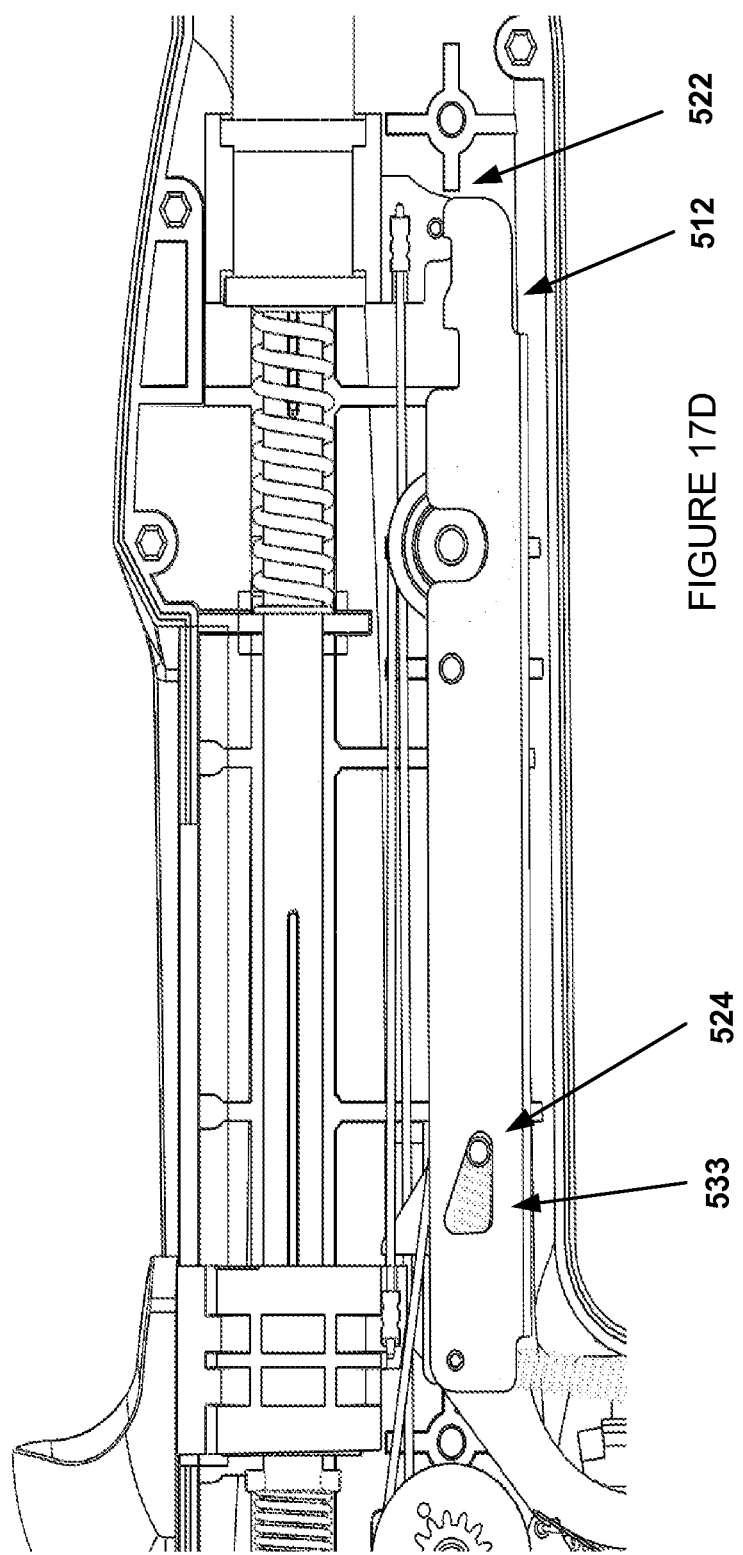

APPARATUS AND METHODS FOR SURGICAL STAPLER CLAMPING AND DEPLOYMENT

CROSS-REFERENCE TO RELATED APPLICATION

This application is a non-provisional application of U.S. Provisional Application No. 61/745,426, filed on Dec. 21, 2012, which is incorporated herein by reference in its entirety.

FIELD OF THE INVENTION

The present invention relates generally to medical devices, and more particularly to endo-cutters or micro-cutters and stapling systems for performing various surgical procedures.

BACKGROUND

Traditionally, surgeons use sutures to close wounds and incisions, attach separate tissue structures to one another, and perform other medical or surgical functions during various surgical procedures or operations. However, proper suturing requires significant skills to perform; in particular, complex suturing procedures can be time-consuming and/or very difficult to perform effectively. Furthermore, suturing may be impractical or unfeasible in certain situations. For example, suturing may be very difficult to perform in minimally-invasive surgical procedures where suturing tools may be required to be inserted through a small opening (often referred to as an access port) to gain access into a patient's body, and then the suturing operation is performed through the small access opening with extension tools to suture the target tissue. In such minimally-invasive surgical procedures, the opening or access port to the surgical site inside the patient may not be large enough to allow effective maneuvering of suturing tools to perform the suturing procedure efficiently and effectively. If access ports were made larger to allow for easier suturing operations, the benefits of minimally-invasive surgery, however, may be significantly reduced or altogether eliminated. Indeed, as surgical technology continues to progress, the size of the access ports required to access surgical sites in the body to perform minimally-invasive procedures correspondingly continues to decrease. Presently, micro-laparoscopy typically utilizes instruments with diameter of about 2 millimeters to about 3 millimeters to perform complex operations; e.g., laparoscopic cholecystectomy and inguinal hernia repair. When instruments of such small diameters are used, the size of the access ports can also be very small. It is common that the access ports can be as small as about 2 millimeters to about 3 millimeters in diameters. The benefits of these advances in surgical technology to the patients are obvious, minimally-invasive procedures can cause less physical trauma to the patient. As such, these minimally-invasive procedures can be performed to greater percentage of patients even if they are not in the best physical condition. In addition, because there is generally less physical trauma involved, the patients may experience less discomfort, the recovery time is typically reduced, and there may be less scarring at the operation site. However, because of restricted access, it can be significantly difficult or even impossible sometimes to perform effective suturing within a patient's body through these small access ports in minimally-invasive procedures. As such, alternatives to suturing are highly desired.

SUMMARY

The present disclosure relates generally to medical devices, and more particularly to endo-cutters or micro-cutters and stapling systems for various surgical procedures. As disclosed, a surgical stapling apparatus is configured to perform stapling and/or cutting operations on a target tissue of a patient. The surgical stapling apparatus comprises of a mode selection switch mechanism to place the apparatus in either a clamping operational phase or a deployment operational phase. In the clamping operational phase, various clamp components are operated to facilitate loading of surgical staples into the stapling apparatus, if staples are not preloaded, placement of the stapling apparatus to a target surgical site, and clamping of target tissue to be stapled and/or cut. In the deployment operational phase, various deployment components are operated to staple and/or cut the target tissue to one or more desired distance intervals to achieve the desired surgical outcome for the patient.

To describe some of the operational details, for example, the surgical stapling apparatus includes a clamp spool member that is coupled to a jaw or stapling assembly (e.g., through a clamp strip, etc.) to execute various clamping operations to prepare the surgical stapling apparatus for deployment (e.g., stapling and/or cutting of target tissue of a patient). The clamping operations include placing the jaw or stapling assembly into various clamping modes. A clamp slide member is coupled to the clamp spool member to drive or move the clamp spool member for various clamping operations. The surgical stapling apparatus also includes deployment spool member to operate or drive various components (e.g., a wedge element to deploy staples, a knife element to cut tissue, etc.) to execute various deployment operations (e.g., deployment of staples, cutting of tissue, etc.). A deployment slide member is coupled to the deployment spool member to drive or move the deployment spool member to execute various deployment operations.

A mode switch mechanism or a mode switch member selectively places the surgical stapling apparatus in either a clamping operational phase or a deployment operational phase.

Operation of a trigger mechanism or a trigger member operates the mode switch mechanism or the mode switch member to selectively place the surgical stapling apparatus in either the clamping operational phase or the deployment operational phase.

When in the clamping operational phase, operation of the trigger member operates the components to execute the various clamping functions. The various clamping functions include placing the surgical stapling apparatus and/or the stapling assembly in a first mode or a trocar mode, a second mode or an open mode, a third mode or a clamping mode, etc.

When in the deployment operational phase, operation of the trigger member operates the components to execute various deployment functions. The various deployment functions include stapling certain amount of target tissue or stapling a target tissue for a certain distance interval. In addition, the various deployment functions include cutting certain amount of target tissue or cutting a target tissue for a certain distance interval.

The surgical stapling apparatus also includes a clamp lock member configured to place or lock the surgical stapling apparatus in various clamping modes. For example, the surgical stapling apparatus includes a clamp slide pin member coupled to the clamp slide member configured to engage with a clamp lock member to place or lock the surgical stapling apparatus in various clamping modes. The clamp lock member includes a first feature to engage with the clamp slide pin member to place or lock the surgical stapling apparatus in a first mode or a trocar mode. The clamp lock member includes a second feature to engage with the clamp slide pin member to place or lock the surgical stapling apparatus in a second mode or an open mode. The clamp lock member includes a third feature to engage with the clamp slide pin member to place or lock the surgical stapling apparatus in a third mode or a clamping mode.

The surgical stapling apparatus also includes a clamp lock release member coupled to the clamp lock member that operates to adjust an angular position or orientation of the clamp lock member to allow release of the clamp slide pin member in a locked position to disengage from one of various clamping modes.

As described from above, the surgical stapling apparatus is configured to perform surgical treatments to a target tissue by operating a trigger member of the surgical stapling apparatus to activate a clamp gear combination, asserting a first trigger-force to place a stapling member in a first mode or trocar mode, asserting a second trigger-force to place the stapling member in a second mode or an open mode, asserting a third trigger-force to place the stapling member in a third mode or a clamp mode, activating a mode selection switch to select a deployment phase; and asserting one or more deployment forces to execute one or more deployment operations. Additionally, asserting a release force to a clamp release member to change an orientation of a clamp lock member to release the stapling member in the first mode or trocar mode, the second mode or open mode or the third mode or clamp mode.

Furthermore, the surgical stapling apparatus is configured to perform surgical treatments to a target tissue by operating a trigger member of the surgical stapling apparatus to activate a clamp gear combination, asserting a first trigger-force to drive a clamp spool member and a clamp slide member combination to place a stapling member in a first mode or trocar mode, asserting a second trigger-force to drive a clamp spool member and a clamp slide member combination to place the stapling member in a second mode or an open mode, asserting a third trigger-force to drive a clamp spool member and a clamp slide member combination to place the stapling member in a third mode or a clamp mode, activating a mode selection switch to select a deployment phase; and asserting one or more deployment forces to drive a deployment spool member and a deployment slide member combination to execute one or more deployment operations. Additionally, asserting a release force to a clamp release member to change an orientation of a clamp lock member to release the stapling member in the first mode or trocar mode, the second mode or open mode or the third mode or clamp mode. The act of changing the orientation or position of the clamp lock member allows a clamp slide pin to disengage from an engaging feature of the clamp lock member.

BRIEF DESCRIPTION OF THE DRAWINGS

The present invention will be readily understood by the following detailed description, taken in conjunction with accompanying drawings, illustrating by way of examples of the invention. The objects and elements in the drawings are not necessarily drawn to scale, proportion, precise orientation or positional relationships; instead, emphasis is focused on illustrating the principles of the invention. The drawings illustrate the design and utility of various features, aspects, or embodiments of the present invention, in which like element are referred to by like reference symbols or numerals. The drawings, however, depict the features, aspects, or embodiments of the invention, and should not be taken as limiting its scope. With this understanding, the features, aspects, or embodiments of the invention will be described and explained with specificity and details through the use of the accompanying drawings in which:

FIG. 3 illustrates the clamp mechanism components without the body and handle of the endo-cutter or micro-cutter and stapling system in accordance with features, aspects, or embodiments of the present invention.

FIG. 4 illustrates additional clamp mechanism components without the body and handle of the endo-cutter or micro-cutter and stapling system in accordance with features, aspects, or embodiments of the present invention.

FIG. 5 illustrates further additional clamp mechanism components without the body and handle of the endo-cutter or micro-cutter and stapling system in accordance with features, aspects, or embodiments of the present invention.

FIG. 12A and FIG. 12B illustrate the deployment mechanism of the endo-cutter or micro-cutter and stapling system in a deployment mode; for example, in a condition ready to deploy an endo-cutter or micro-cutter in accordance with features, aspects, or embodiments of the present invention.

FIG. 13A and FIG. 13B illustrate the deployment mechanism of the endo-cutter or micro-cutter and stapling system in a first deployed mode; for example, a first trigger-squeeze in the deployment mode.

FIG. 14A and FIG. 14B illustrate the deployment mechanism of the endo-cutter or micro-cutter and stapling system in a second deployed mode; for example, a trigger-release state after the first deployed mode.

FIG. 15A and FIG. 15B illustrate the deployment mechanism of the endo-cutter or micro-cutter and stapling system in a third deployed mode; for example, a second trigger-squeeze after the second deployed mode.

FIG. 16A and FIG. 16B illustrate the deployment mechanism of the endo-cutter or micro-cutter and stapling system in a fourth deployed mode; for example, a trigger-release state after the third deployed mode.

FIG. 17A and FIG. 17B illustrate a back-view of the endo-cutter or micro-cutter and stapling system illustrating that the mode switch mechanism has been reset to place the endo-cutter or micro-cutter and stapling system in the first mode or trocar mode in accordance with features, aspects, or embodiments of the present invention.

FIG. 17C and FIG. 17D illustrate a side-view of the endo-cutter or micro-cutter and stapling system illustrating that the mode switch mechanism has been reset to place the endo-cutter or micro-cutter and stapling system in the first mode or trocar mode in accordance with features, aspects, or embodiments of the present invention

DETAILED DESCRIPTION

Figure 1:
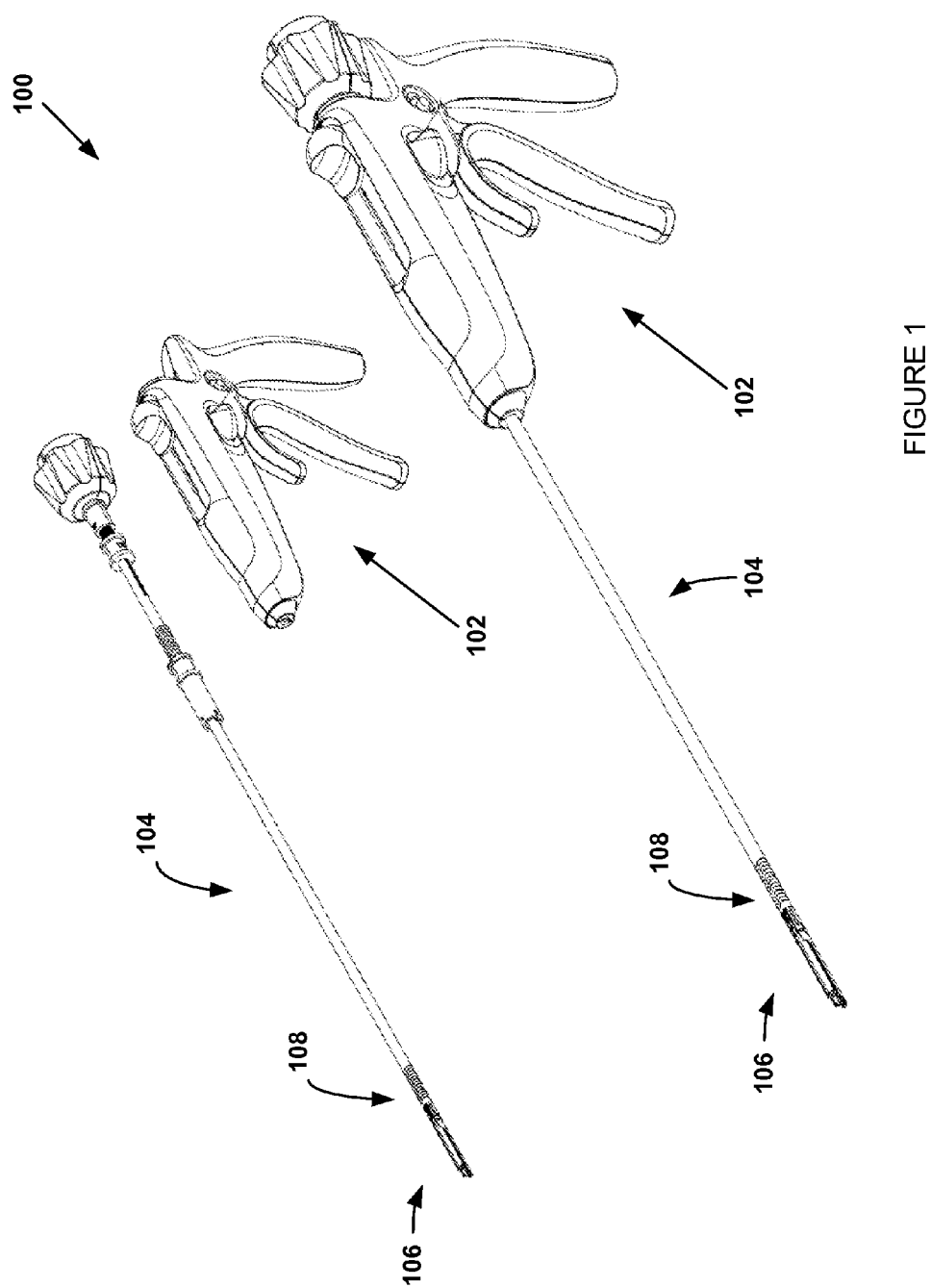
FIG. 1 illustrates examples of endo-cutter or micro-cutter and stapling systems where the clamp and deploy mechanisms in accordance with features, aspects, or embodiments of the present invention may be used to clamp, cut and staple tissue at surgical sites of a patient.

FIG. 1 illustrates examples of endo-cutter or micro-cutter and stapling systems 100 that can be alternatives or replacements to suturing. In particular, these endo-cutter or micro-cutter and stapling systems 100 are especially useful as alternatives or replacements to suturing in minimally-invasive surgical procedures. As illustrated in the figure, the operation of cutting and stapling is performed through a long slim shaft 104. The actual operations of clamping, cutting, and stapling of tissue are performed at the distal-end 106 of the shaft 104, and the control operations of these procedures are performed at the handle assembly 102. The distal-end 106 may include a stapling system comprising of a staple channel and a staple anvil, which are illustrated in FIG. 1. The staple channel may include a staple holder or a staple cartridge for holding staples. The staple anvil deforms the staples as they are deployed. As the staples are deployed, the staples pierce the target tissue and the staple anvil deforms the staples to secure the staples against the target tissue. Further illustrated, the shaft at the distal-end may be substantially flexible and may be articulated. For example, near the distal-end of the shaft may include an articulated section 108. Various versions of the endo-cutter or micro-cutter stapling systems may have non-articulated rigid shafts, while other versions may include substantially flexible or flexible portions that can be articulated. These and other features allow such examples of endo-cutter or micro-cutter and stapling systems (e.g., MICROCUTTER XPRESS™ and MICROCUTTER XCHANGE™, which are designed and manufactured by Cardica Inc. of U.S.A.) to be ideally suited as alternatives or replacements to suturing. Greater detailed discussions of endo-cutter or micro-cutter stapling systems are described in U.S. patent application Ser. No. 12/323,309, filed on Nov. 25, 2008; U.S. patent application Ser. No. 12/400,760, filed on Mar. 9, 2009; U.S. patent application Ser. No. 12/400,790, filed on Mar. 9, 2009; U.S. patent application Ser. No. 12/477,065, filed on Jun. 2, 2009; U.S. patent application Ser. No. 12/787,708, filed on May 26, 2010; U.S. patent application Ser. No. 13/093,791, filed on Apr. 25, 2011; U.S. patent application Ser. No. 12/477, 302, filed on Jun. 3, 2009; U.S. patent application Ser. No. 12/489,397, filed on Jun. 22, 2009; U.S. patent application Ser. No. 12/612,614, filed on Nov. 4, 2009; U.S. patent application Ser. No. 12/840,156, filed on Jun. 20, 2010; U.S. patent application Ser. No. 13/028,148, filed on Feb. 15, 2011; U.S. patent application Ser. No. 13/048,674, filed on Mar. 15, 2011; U.S. patent application Ser. No. 13/094,716, filed on Apr. 26, 2011; U.S. patent application Ser. No. 13/094,805, filed on Apr. 26, 2011; U.S. patent application Ser. No. 13/093,743, filed on Apr. 25, 2011; U.S. patent application Ser. No. 13/105,799, filed on May 11, 2011; and U.S. patent application Ser. No. 13/294,160, filed on Nov. 10, 2011, all of which are incorporated herein by reference.

Figure 2A:
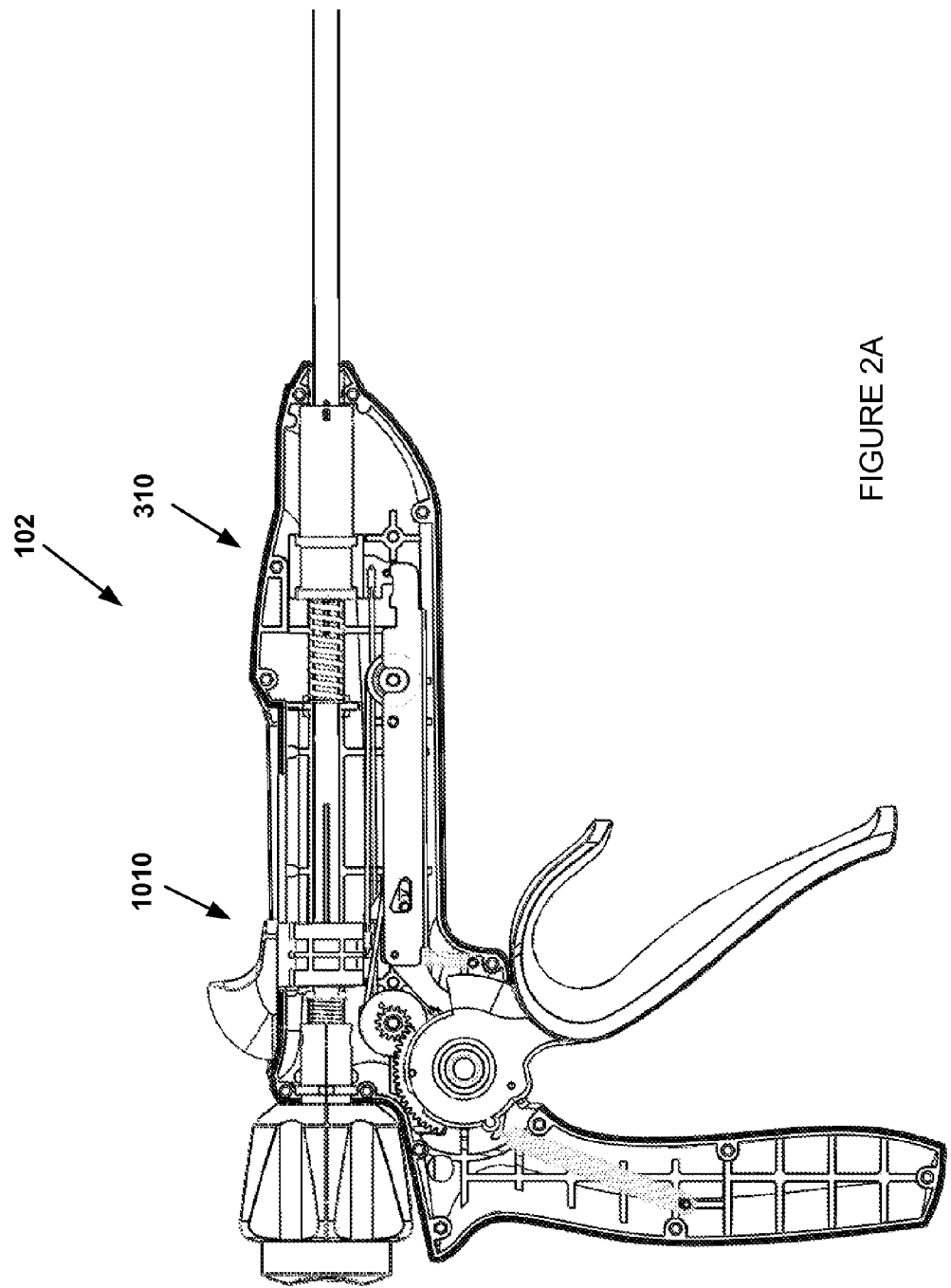
FIG. 2A through FIG. 2C illustrates an exposed view of the body, handle, and trigger of an endo-cutter or micro-cutter and stapling system where the clamp and deploy mechanisms are illustrated.
Figure 2B:
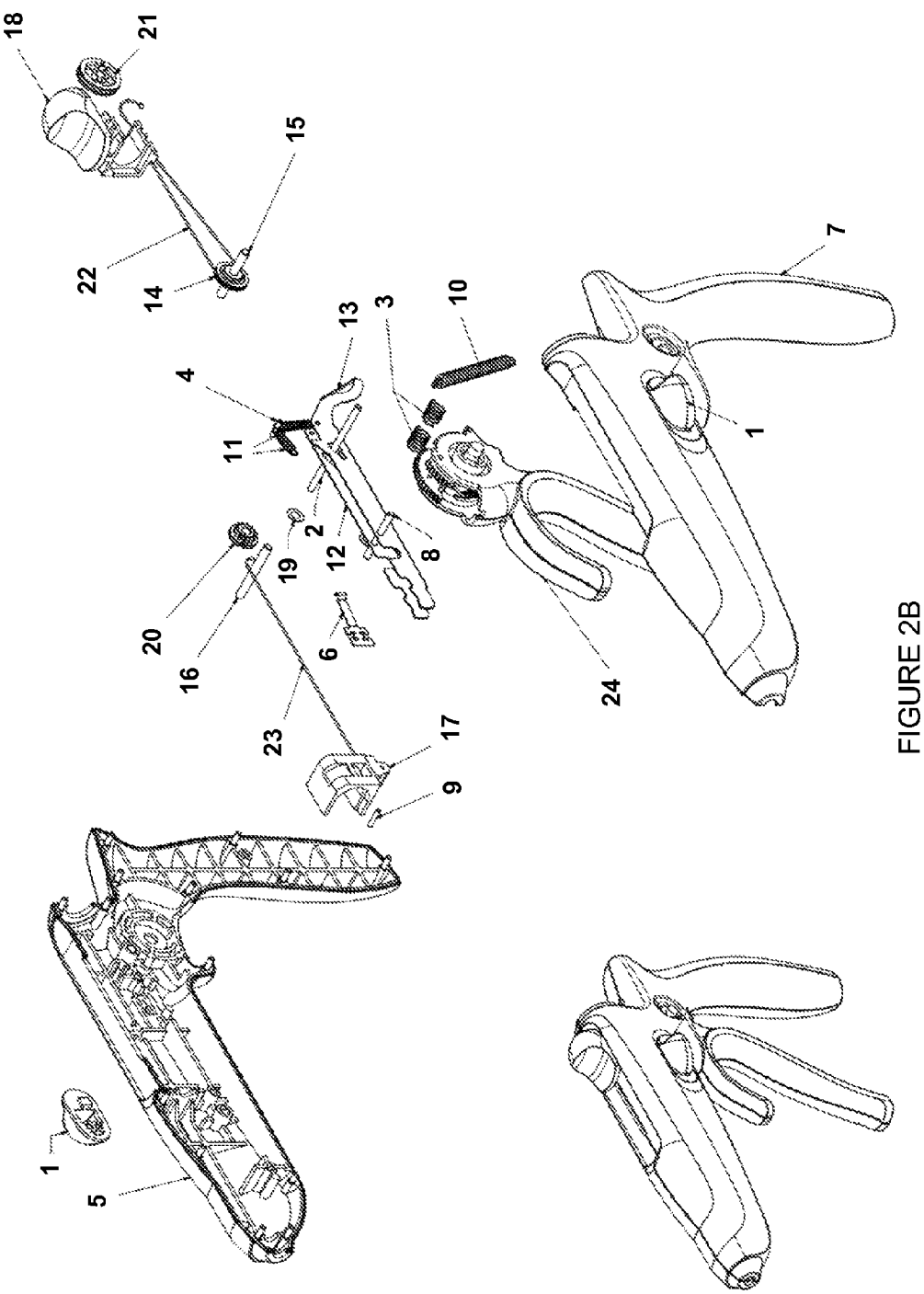
Figure 2C:
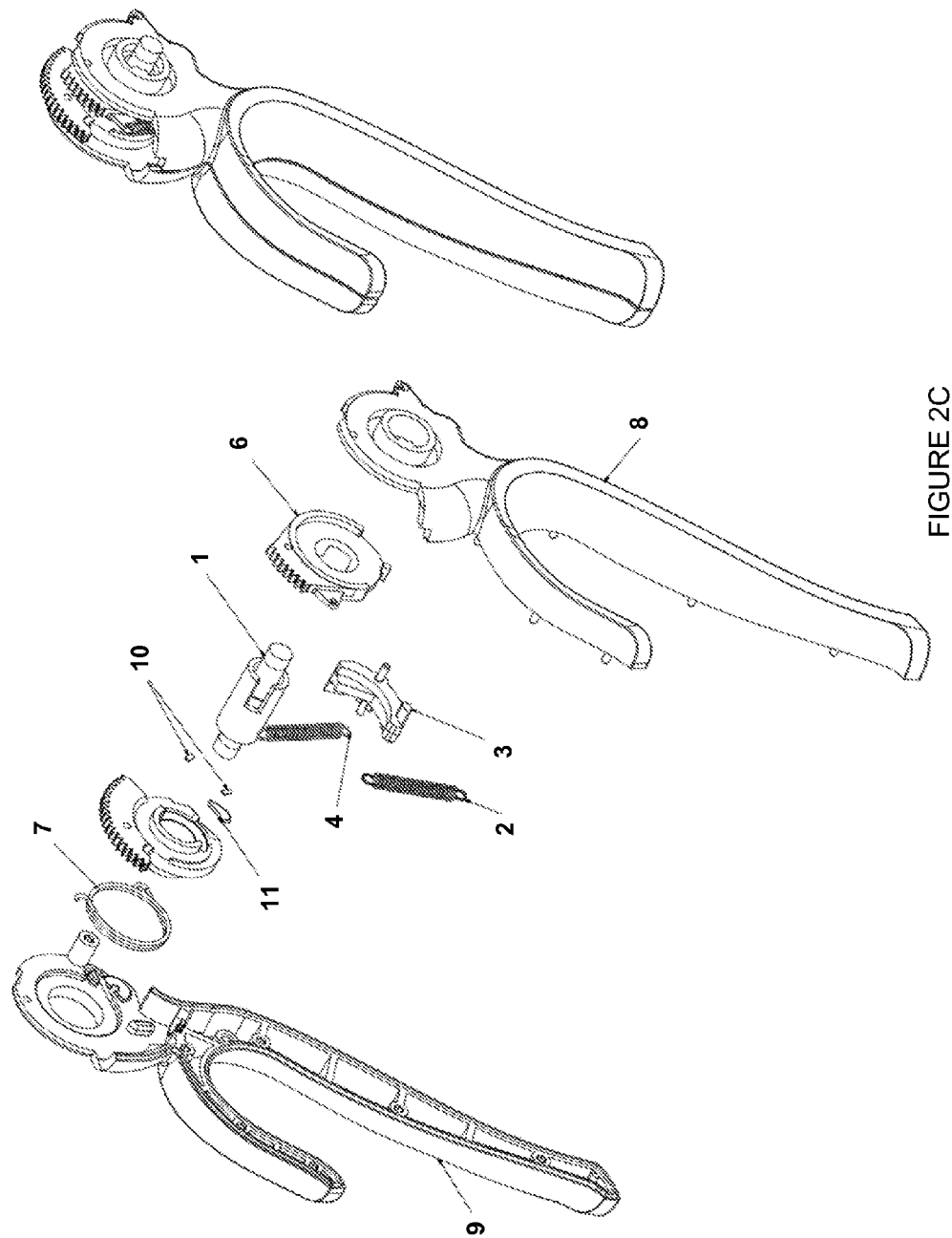

FIG. 2A through FIG. 2C illustrate exposed and exploded views of the body, handle, and trigger elements of one example of endo-cutter or micro-cutter and stapling system 100 handle assembly 102 where the clamp and deployment mechanisms (e.g., 310 and 1010 in FIG. 2A) are illustrated. In addition, some of the piece-part components of the handle assembly 102 are separately marked with reference numerals for ease of illustration and discussion, as pertain to and illustrated in FIG. 2B and FIG. 2C. For ease of discussion and additional reference, component or parts identification to the referenced numerals associated with FIG. 2B are: (1)—Release; (2)—Pin (Release); (3)—Spring (Mode Button); (4)—Pin (Release Spring); (5)—Handle (Right); (6)—Handle (Left); (7)—Pin (Clamp Lock); (8)—Pin (Clamp Slide); (9)—Spring (Trigger); (10)—Spring (Release); (11)—Clamp Lock; (12)—Clamp Lock Tab; (13)—Deployment Pulley; (14)—Pin (Deployment Pulley); (15)—Pin (Gear); (16)—Slide (Clamp); (17)—Slide (Deployment); (18)—Washer (Gear); (19)—Clamp Pulley & Gear; (20)—Deploy Pulley & Gear; (21)—Cable Deploy; (22)—Cable Clamp; (23)—Trigger Subassembly; (24)—Adhesive; and (25)—Grease. For ease of discussion and additional reference, component or parts identification to the referenced numerals associated with FIG. 2C are: (1)—Mode Button; (2)—Spring (Ratchet); (3)—Ratchet; (4)—Spring (Trigger Clamp Gear); (5)—Trigger Gear (Deploy); (6)—Trigger Gear (Clamp); (7)—Spring (Trigger Deploy Gear); (8)—Trigger (Left); (9)—Trigger (Right); and (10)—Adhesive.

Figure 9:
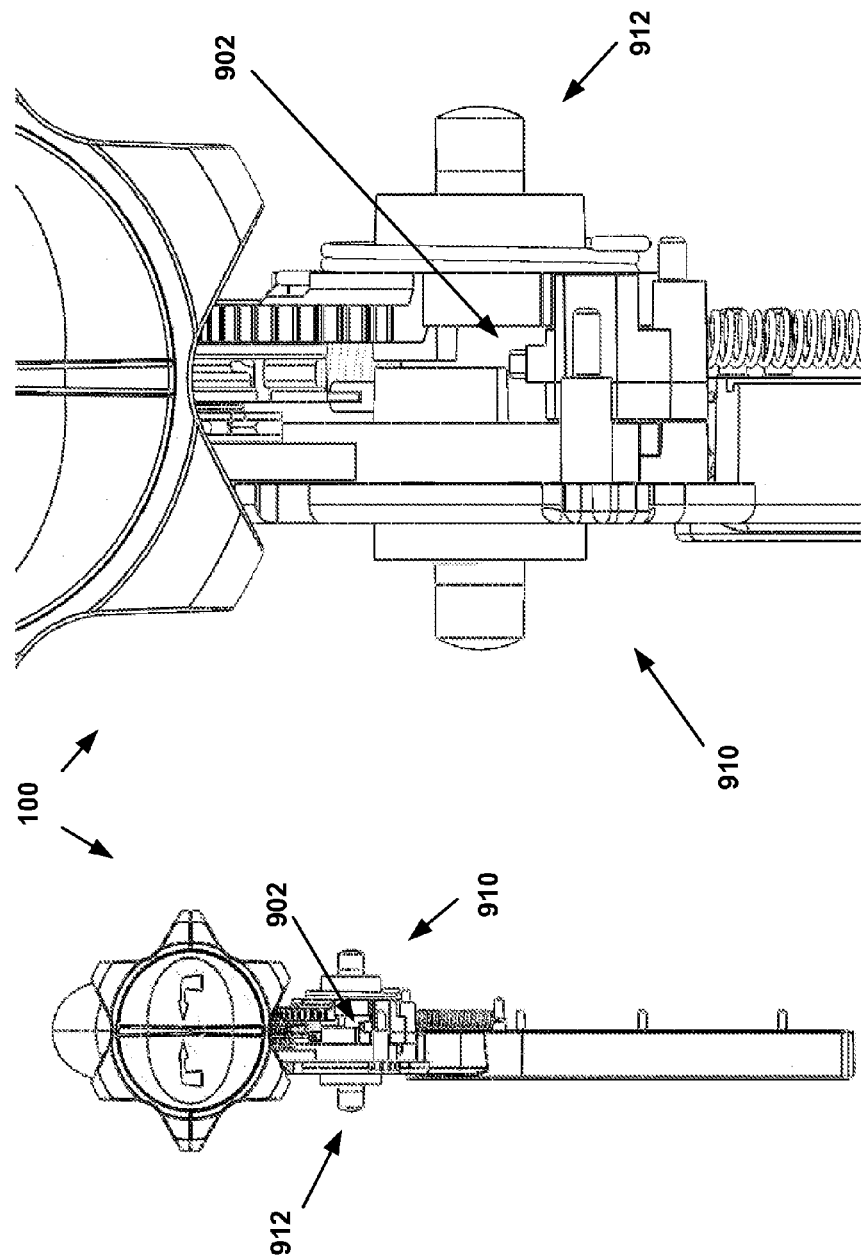
FIG. 9A and FIG. 9B illustrate a back view of the endo-cutter or micro-cutter and stapling system where a mode switch mechanism is illustrated in accordance with features, aspects, or embodiments of the present invention.
Figure 11:
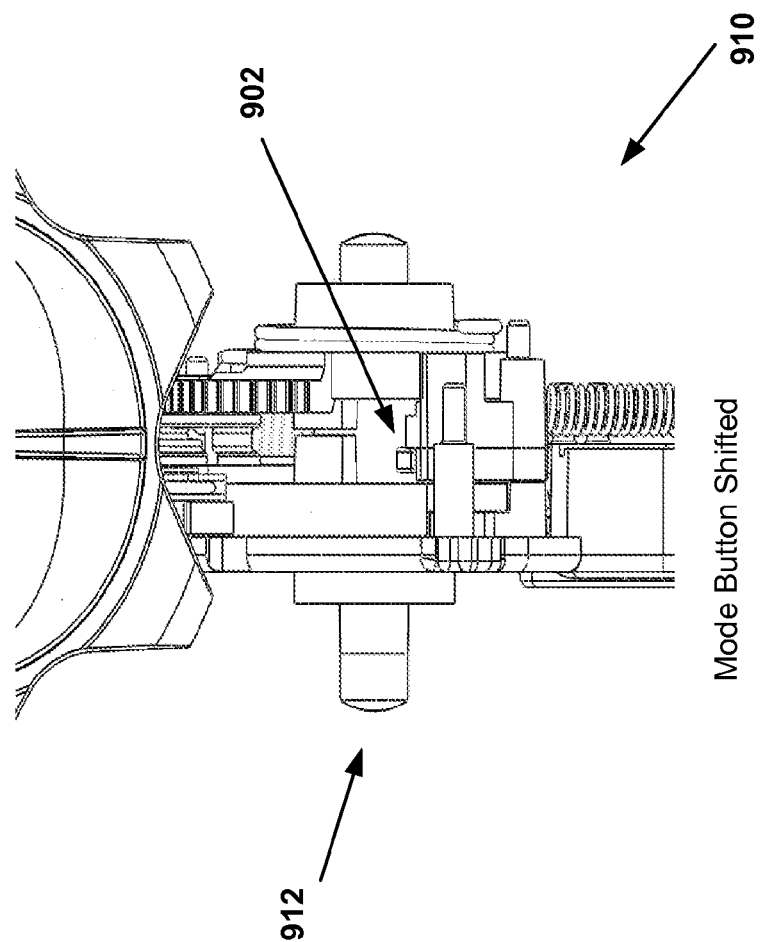
FIG. 11 illustrates illustrate a back view of the endo-cutter or micro-cutter and stapling system where a mode switch mechanism has been activated to place the endo-cutter or micro-cutter and stapling system in a deployment mode in accordance with features, aspects, or embodiments of the present invention.

As can be depicted from the FIG. 2A, FIG. 2B, and FIG. 2C, the system includes a trigger 302 in the handle assembly 102 to activate the gear system 300 (as indicated in FIG. 3A) that in turn operate either the clamp or deploy mechanisms (e.g., 310, 1010), depending on which operational mode is selected by a mode switch mechanism 910, 912 (as illustrated in FIG. 9A, FIG. 9B, and FIG. 11).

FIG. 3, FIG. 4, and FIG. 5 illustrate the clamp mechanism components 310 without the body and handle cover of the endo-cutter or micro-cutter and stapling system 100 for ease of illustration and discussion. As can be appreciated from the figures, the trigger member 302 activates a set of clamp gears 300 which in turn pulls on a clamp cable member 322 that asserts a pull force onto a clamp slide member 332 and clamp spool member 342 combination. To be discussed in further detail, as the clamp slide member 332 and clamp spool member 342 combination is either pulled back by the clamp cable member as may be appreciated from the illustration of FIG. 3 or pushed forward by a spring member 412 as illustrated in FIG. 4, the position of the slide member 332 and spool member 342 combination may be locked into various clamping mode positions (e.g., first mode, second mode, or third mode) by the clamp lock member 512 as illustrated in FIG. 5. The slide member 332 and spool member 342 can be locked in various positions as a clamp slide-pin member 522 travels either backward (as pulled by the cable member 322) or forward (as pushed by the spring member 412) along the clamp lock member 512. The clamp slide-pin 522 may rest on the clamp lock member 512 or in the various notches or detents (e.g., 513, 523, etc.) that are on the clamp lock member 512. The combination of the slide member 332, spool member 342, and clamp slide-pin member 522 are configured to operate in concert to hold the jaws (e.g., the staple channel and staple anvil) of the stapling member 106 in various operational modes or positions—such as, a first mode or trocar mode, a second mode or open mode, or a third mode or clamping mode (the stapling member of the distal-end 106 is illustrated in FIG. 1).

As illustrated in FIG. 5, the clamp slide-pin member 522 is resting near the tip of the clamp lock member 512 (e.g., in a first mode or trocar mode), not in any one of the notches or detents (e.g., 513, 523). These various clamp modes (e.g., first mode or trocar mode, second mode or open mode, or third mode or clamping mode, etc.) are associated with various clamp operational modes of the clamp member 106 or stapling member 106 located at substantially the distal portion of the long slim shaft 104 of the endo-cutter or micro-cutter and stapling system 100 as illustrated in FIG. 1.

Typically, in a first state or neutral state, the clamp mechanism components 310 set the clamp or stapling member 106 in a first mode or trocar mode. In this mode, the jaws of the clamp member 106 of the cutter and staple system 100 may be in a smallest or most compact configuration, which allows it to be inserted through a small opening or access port for executing cutting and stapling procedures in minimally invasive surgical operations. As mentioned previously, for example, the clamp 106 may be comprised of stapling jaw components including a staple channel (with a staple holder or staple cartridge) and a staple anvil. As can be observed in FIG. 6, the slide member 332 is substantially at its most extended position and the clamp slide-pin member 522 is positioned or resting at substantially the tip of the clamp lock member 512. Also, the trigger member 302 is in its released-state or extended-state, ready to be use—such as ready to be squeezed or activated by a surgeon.

Figure 6:
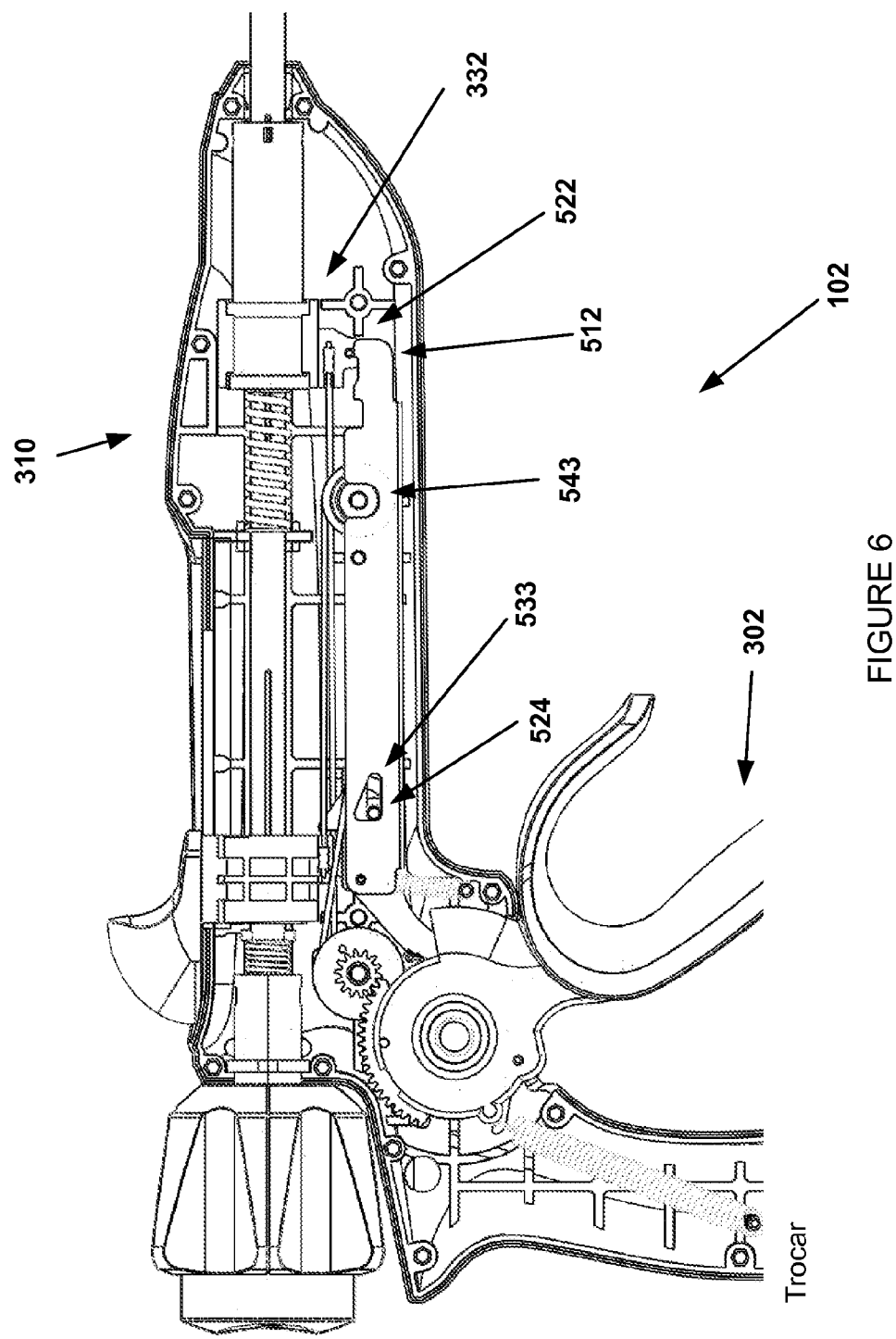
FIG. 6 illustrates the clamp mechanism in a first mode; for example, trocar mode in accordance with features, aspects, or embodiments of the present invention.
Figure 7:
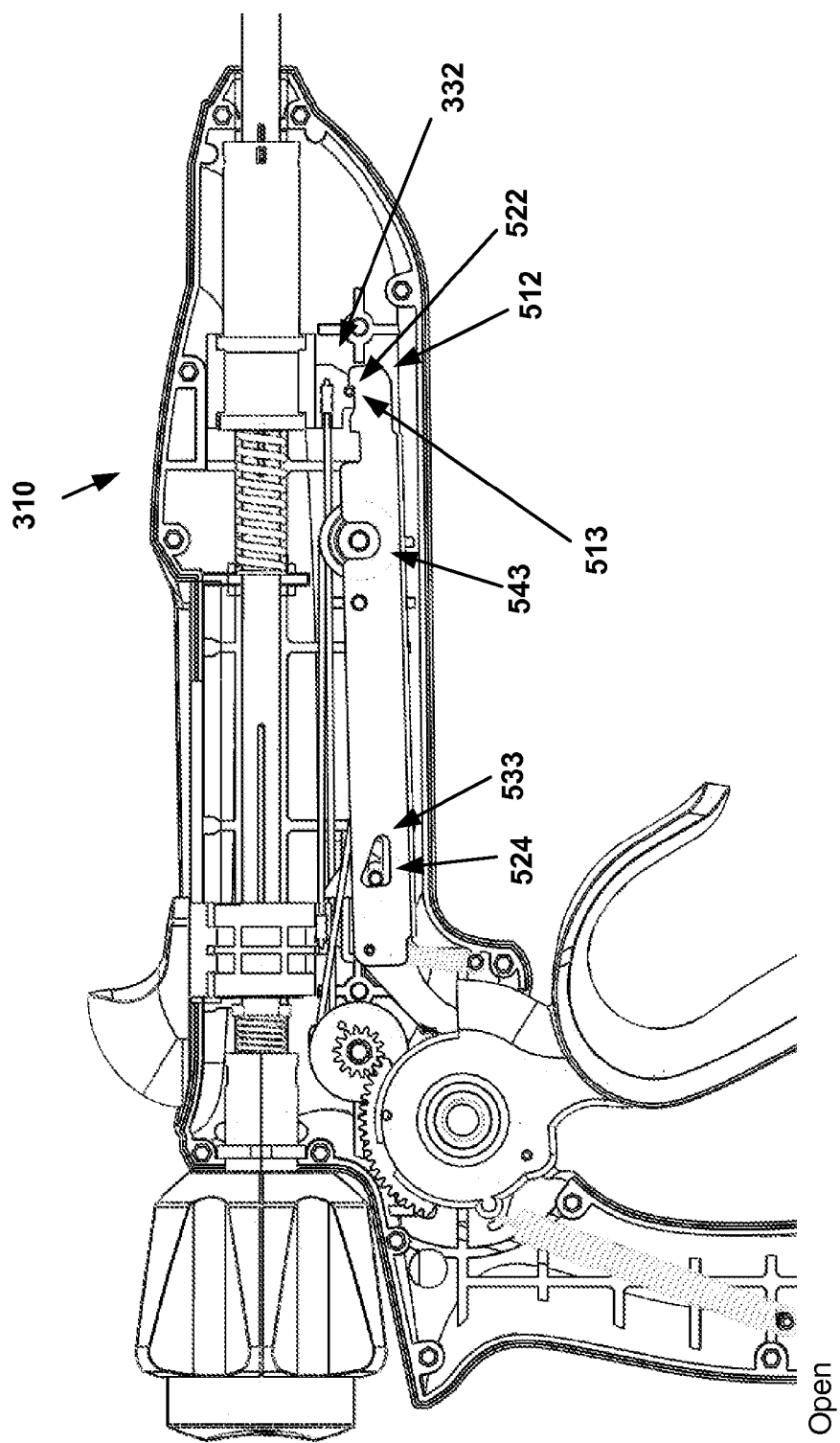
FIG. 7 illustrates the clamp mechanism in a second mode; for example, open mode in accordance with features, aspects, or embodiments of the present invention.

The clamp mechanism components 310 are activated by a partial-squeeze of the trigger member 302, as illustrated in FIG. 7. The partial-squeeze of the trigger member 302 activates the clamp gears 300 to rotate and asserts a pull force onto the slide member 332 to slide backwards toward the proximal portion of the cutter and stapling system 100. As illustrated in FIG. 7, the slide member 332 has been pulled back and the clamp slide-pin member 522 is resting in a first notch or first detent 513 on the clamp lock member 512. The backward movement of the slide member 332 asserts a pull force on the components of the jaws of the clamp (e.g., stapling members: staple channel and staple anvil—not shown) which causes the jaws of the clamp to open in this second mode or open mode. In this second mode or open mode, staples or staple cartridges can be loaded into the clamp or stapling system (e.g., staple channel & staple cartridge combination). Also, after the cutting and stapling system is inserted into the target operational site, in the second mode or open mode, the clamp (106) can be positioned to grasp tissue for stapling. Further illustrated in FIG. 7 is that a clamp pin-release member or clamp lock release member 524 is in a second-level position in a substantially triangular slot 533 or the first slot 533, on the clamp lock member 512, as compared to a first-level position, when the clamp mechanism components 310 are in a first mode or trocar mode as illustrated in FIG. 6. The clamp pin-release member 524 in a second-level position may cause the clamp lock member 512 to be in a substantially angular orientation as compared to the clamp release-pin 524 in a first-level position. Alternatively, the clamp pin-release member 524 in a second-level position may cause the clamp lock member 512 to be in a substantially greater angular orientation as compared to the pin-release member 524 in the first-level position. When the clamp release-pin 524 is in the first-level position, the clamp lock member 512 may be oriented in a substantially horizontal orientation. Whereas, when the clamp release-pin 524 is in the second-level position, the clamp lock member 512 may be oriented in a slightly or substantially angular orientation or in a substantially non-horizontal orientation.

Figure 8:
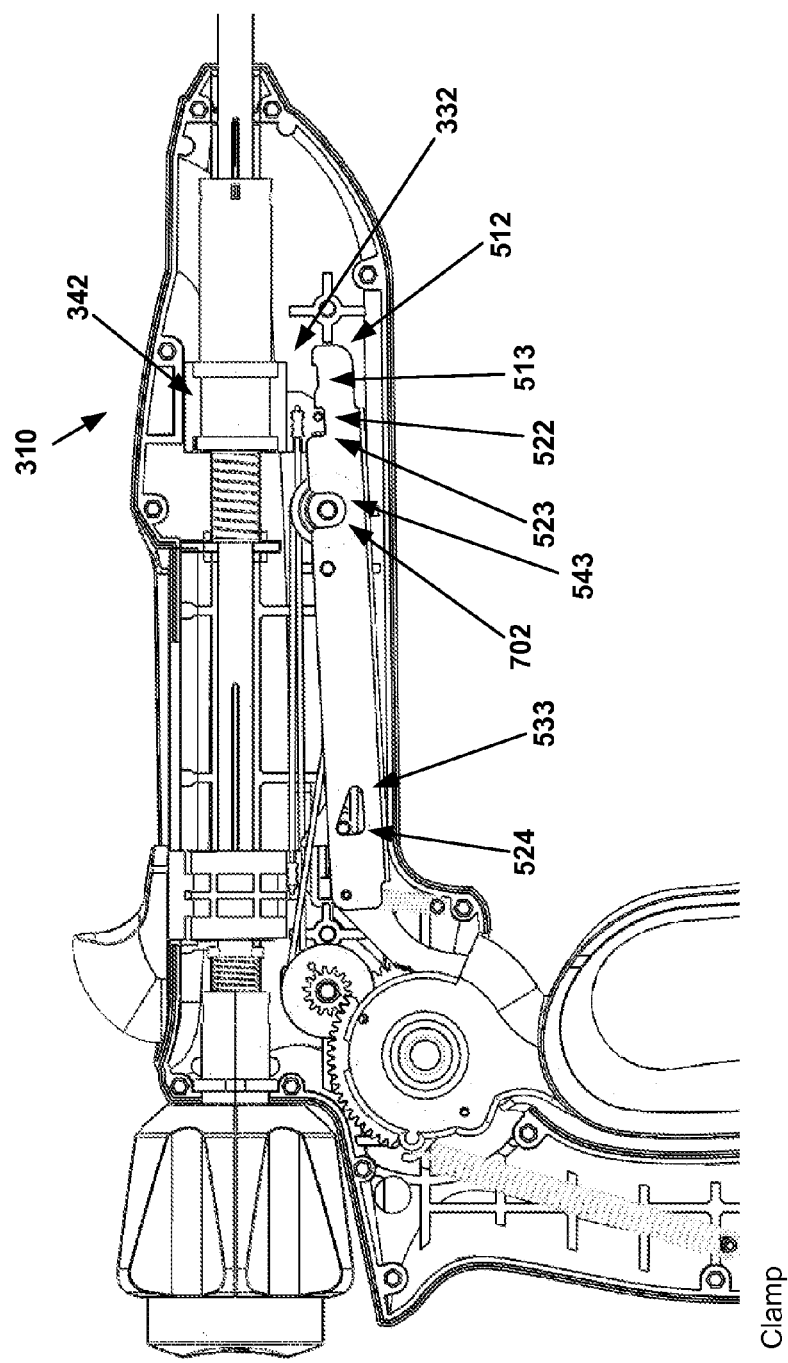
FIG. 8 illustrates the clamp mechanism in a third mode; for example, clamping mode in accordance with features, aspects, or embodiments of the present invention.

FIG. 8 illustrates the clamp mechanism 310 components in a third mode or clamping mode as caused by a full-squeeze or full-activation of the trigger member 302. The full-squeeze of the trigger member 302 further advances the clamp gears 300 that winds up the cable member 322, which further pulls the slide member 332 and spool member 342 combination backwards further towards the proximal portion of the cutter and stapling system 100. The backward movement of the slide member 332 causes the clamp slid-pin member 522 to travel into a second notch or second detent 523 of the clamp lock member 512. In this mode, the spool member 342 which connects or couples to the components of the jaws of the clamp 106 (e.g., stapling members) causes the jaws of the stapling members 106 to clamp onto the tissue that is ready to be stapled. In this position, in the second notch or second detent 523, the jaws are secured or locked in clamping mode. Further illustrated in FIG. 8, the pin-release member 524 is in a third-level position. In this third-level position, the clamp lock member 512 is at a substantial angular orientation, in which the clamp lock member has pivoted about a clamp pin-lock member 702 in a third notch or third detent 543. In this position, the clamp lock member 512 securely holds the clamp slide-pin 522 in the second notch or second detent 523 of the clamp lock member 512. To release the jaws of the clamp or the stapling member 106, the clamp lock member 512 can be moved to "unlock" or "release" the clamp slide-pin member 522 from the second notch or second detent 523 by adjusting or pushing forward the pin-release member or clamp lock release member 524 in the triangular slot 533. The releasing adjustment or movement of the pin-release member 525 causes the clamp lock member 512 to move or position itself in a substantially "opposite" angular orientation, which allows the clamp slide-pin member to be released from the second notch 523 as the spring member 412 pushes the clamp spool member 342 and clamp slide member 332 forward. Similarly, the clamp slide-pin member 522 can be released from the first notch 513 in a substantially similar manner.

With the clamp mechanism 310 is in the third mode and target tissue is clamped, the next phase of the operation is ready to be deployed. FIG. 9A and FIG. 9B illustrate a backside view of an endo-cutter or micro-cutter and stapling system 100 where a mode switch mechanism 910 and a mode selection member 912 are illustrated. A stand-off member 902 is shown to engage the clamp gears 300 that drive the clamp mechanism 310.

Figure 10:
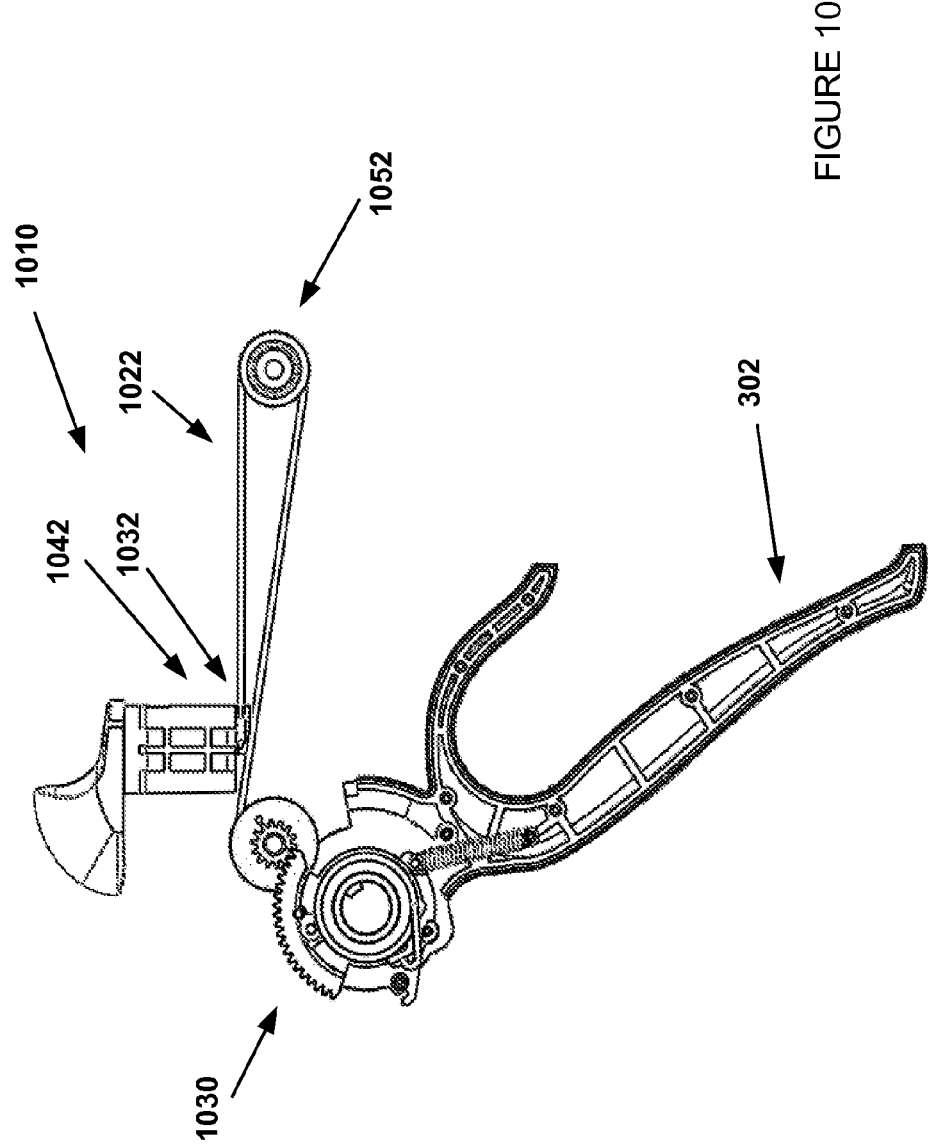
FIG. 10 illustrates the deploy mechanism components without the body and handle of the endo-cutter or micro-cutter and stapling system in accordance with features, aspects, or embodiments of the present invention.

FIG. 10 illustrates the deploy mechanism components 1010 that are used to deploy or drive an endo-cutter or micro-cutter 100 to cut target tissue. Cutting and stapling of target issue may occur at substantially the same time or the operations may be separated by a substantially small time incremental period. As illustrated in FIG. 10, the deploy mechanism 1010 comprises of a set of deploy gears 1030, a deployment cable member 1022, a combination of deployment slide member 1032 and a deployment spool member 1042, and a deploy pulley member 1052. FIG. 11 illustrates a backside-view of an endo-cutter or micro-cutter and stapling system where a mode switch mechanism 910 has been activated to place the endo-cutter or micro-cutter and stapling system 100 in a deployment mode. For example, a mode switch button 912 has been pushed or activated to move the stand-off member 902 of the mode switch mechanism 910 to engage the gears 1030 of the deploy mechanism 1010, while disengaging with the clamp drive gears 300 of clamp mechanism 310. Once the deploy mechanism 1010 is engaged, activation of the trigger member 302 activates the gears 1030 of the deploy mechanism 1010 which advances or drives the endo-cutter or micro-cutter 100 to cut target tissue. Additionally, the deployment mechanism 1010 may also advances or drives the endo-cutter or micro-cutter 100 to staple target tissue.

FIG. 12A and FIG. 12B illustrate the deployment mechanism components of the endo-cutter or micro-cutter and stapling system in a deployment mode; for example, in a condition ready to deploy an endo-cutter or micro-cutter. As illustrated in FIG. 12B, a deploy ratchet member 1212 engages a first tooth 1242 of a first deploy gear 1214. FIG. 13A and FIG. 13B illustrate the deployment mechanism components of the endo-cutter or micro-cutter and stapling system in a first deployed mode; for example, a first trigger-squeeze in the deployment mode. As the trigger member 302 is squeezed or activated, the deploy ratchet member 1212 urges or advances the first deploy gear 1214, as illustrated in FIG. 13B. The first deploy gear 1214 acts on a second deploy gear 1216 which winds and pulls on a deploy cable member 1222. The deploy cable member 1222 pulls on the combination of deploy slide member 1032 and deploy spool member 1042 to advance the combination to a first deployed position, illustrated in FIG. 13A. The movement of the combination advances the components associated with the endo-cutter or micro-cutter (such as a deployment strip member 1252, a knife member (not shown), etc.) to a first position; cutting targeted tissue to a certain distance or interval. Additional deployment members may also be activated, such as a wedge member (not shown) to drive and deploy staples in the clamp member 106 to correspondingly staple the targeted tissue to a certain distance or interval.

FIG. 14A and FIG. 14B illustrate the deployment mechanism components of the endo-cutter or micro-cutter and stapling system in a second deployed mode; for example, a trigger-release state after the first deployed mode. In FIG. 14A, it is illustrated that the trigger member 302 is released, which causes the deploy ratchet member to return or retreat and engages the second tooth 1244 of the first deploy gear 1214. In this position, the deploy mechanism 1010 is ready for further deployment.

FIG. 15A and FIG. 15B illustrate the deployment mechanism components of the endo-cutter or micro-cutter and stapling system in a third deployed mode; for example, a second trigger-squeeze after the second deployed mode. As illustrated in FIG. 15A, the trigger member 302 is squeezed to advance the first deploy gear 1214, which is illustrated in FIG. 15B. The advancement or rotation of the first deploy gear advances or rotates the second deploy gear 1216 in an opposite direction, which winds or pulls on the deploy cable member 1222. The deploy cable member 1222 winds around a deploy pulley 1052 and pulls the combination of deploy slide member 1032 and deploy spool member 1042. The deployment member combination (1032 and 1042) is moved forward or advanced to a second deployed position, as illustrated in FIG. 15A. The movement of the deployment member combination (1032 and 1042) advances or drives the components associated with the endo-cutter or micro-cutter further forward (e.g., a deployment strip member 1252, a knife member (not shown), etc.), thus further cutting the targeted tissue. Additional deployment members may also be activated, such as a wedge member (not shown) to drive and deploy staples in the clamp member 106 to correspondingly staple the targeted tissue to a certain distance or interval.

FIG. 16A and FIG. 16B illustrate the deployment mechanism components of the endo-cutter or micro-cutter and stapling system in a fourth deployed mode; for example, a trigger-release state after the third deployed mode. As illustrated in FIG. 16A, the trigger member 302 is released, which allows the deploy ratchet member 1212 to return or retreat. The return of the deploy ratchet member 1212 allows it to engage a third tooth 1246 on the first deploy gear 1214. The engagement of the deploy ratchet 1212 with the third tooth 1246 on the first deploy gear 1214 may provide sufficient adjustments to the engagement of the mode switch mechanism 910 to allow it to reset. For example, the adjustment may allow the mode switch mechanism 910 and/or the mode switch selection member 912 to reset or reengage the mechanisms and components of deploy and clamp operations to the first mode (e.g., clamp mechanism first mode).

Figure 17A:
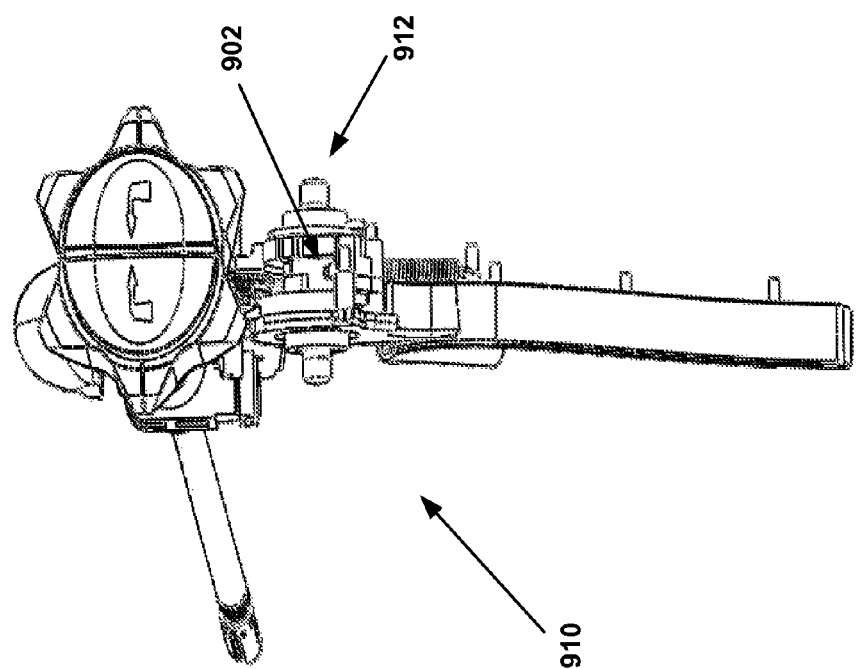

The adjustment and engagement of the mode switch mechanism 910 and/or the mode switch selection member 912 may be triggered by the third tooth pushing on the deployment ratchet 1212 as the ratchet engages with the third tooth 1246. The third tooth 1246 may be irregular-shaped or has a shape that is substantially different than the shape of the first tooth and/or second tooth of the first deploy gear 1214. The mode switch mechanism 910 may be spring-loaded, such that the engagement of the deploy ratchet 1212 with the third tooth 1246 provides sufficient adjustment or movement to allow the spring-loaded mode switch mechanism 910 to reset. The resetting of the mode switch mechanism allows the stand-off 902 member to return to a position where the clamp gears 300 of the clamp mechanism 310 is engaged and in state of the first mode (clamp mechanism first mode), as illustrated in FIG. 17A and FIG. 17B.

Figure 17C:
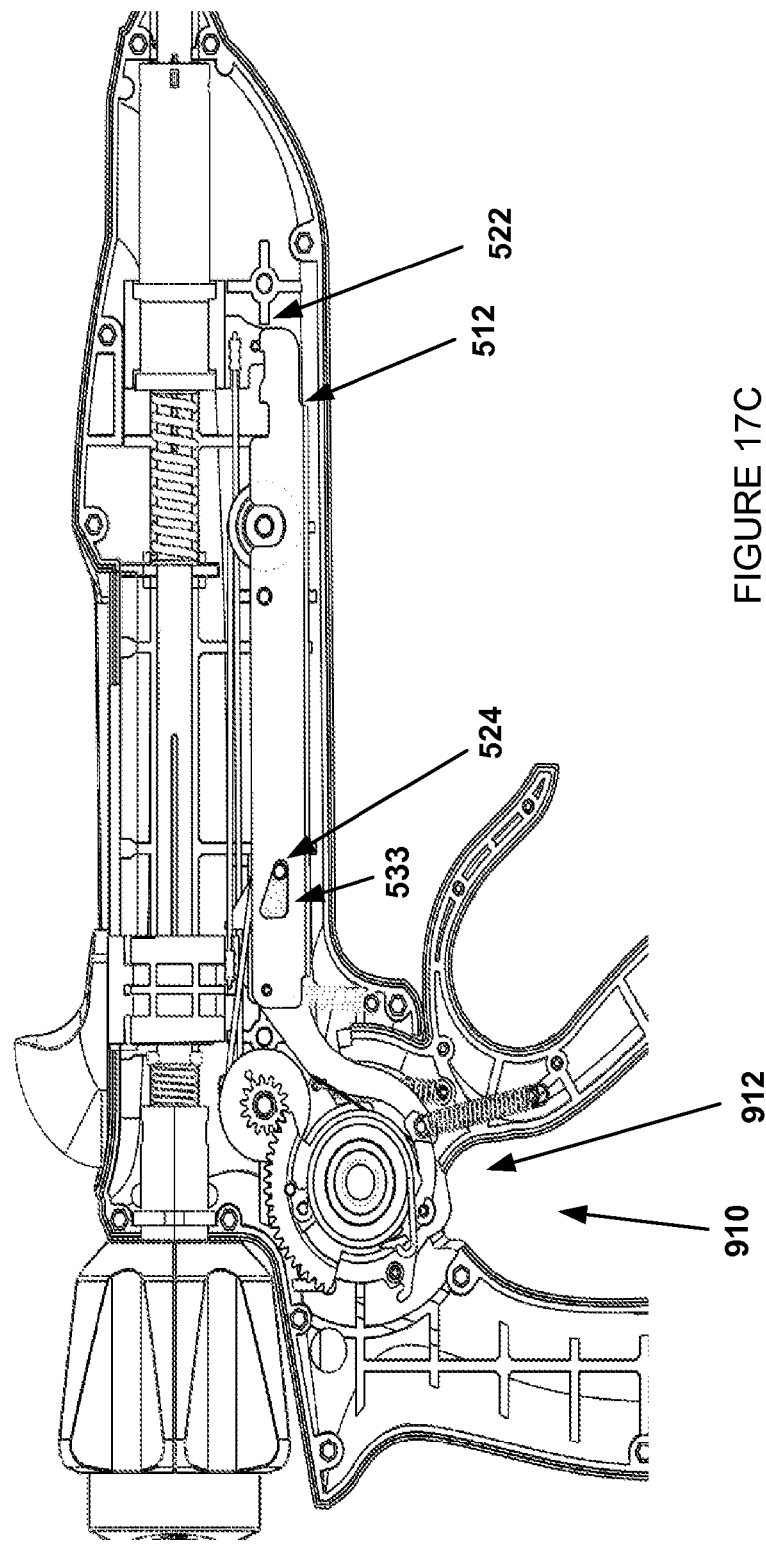

FIG. 17C and FIG. 17D illustrate side-views of the endo-cutter or micro-cutter and stapling system 100 illustrating that the mode switch mechanism 910, 912 has been reset to place the endo-cutter or micro-cutter and stapling system 100 in the first mode or trocar mode. As may be appreciated from the illustrations, the clamp slide pin member 522 is positioned or resting near the tip of the clamp lock member 512. Also, the clamp pin-release member 524 is positioned or resting in the first-level position in the substantially triangular-shaped slot 533 in the clamp lock member 512. The first-level position may allow the clamp lock member 512 to be in a substantially horizontal level, orientation, or position.

Figure 18A:
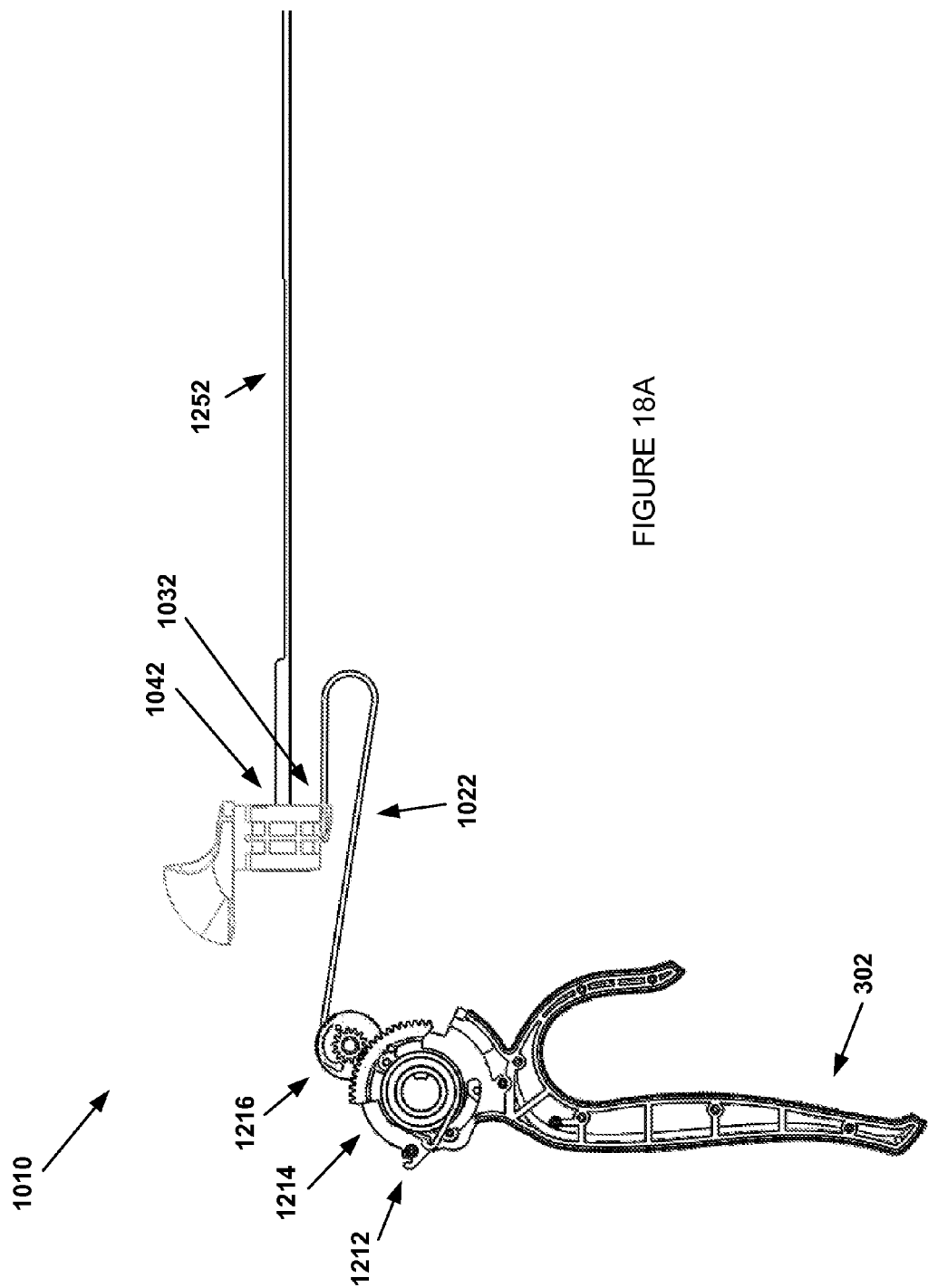
FIG. 18A and FIG. 18B illustrate the deploy mechanism components in a deployed state illustrating that components or accessories (e.g., endo-cutter or micro-cutter) attached or coupled to the deploying components have been deployed or advanced to their deployed state.
Figure 18B:
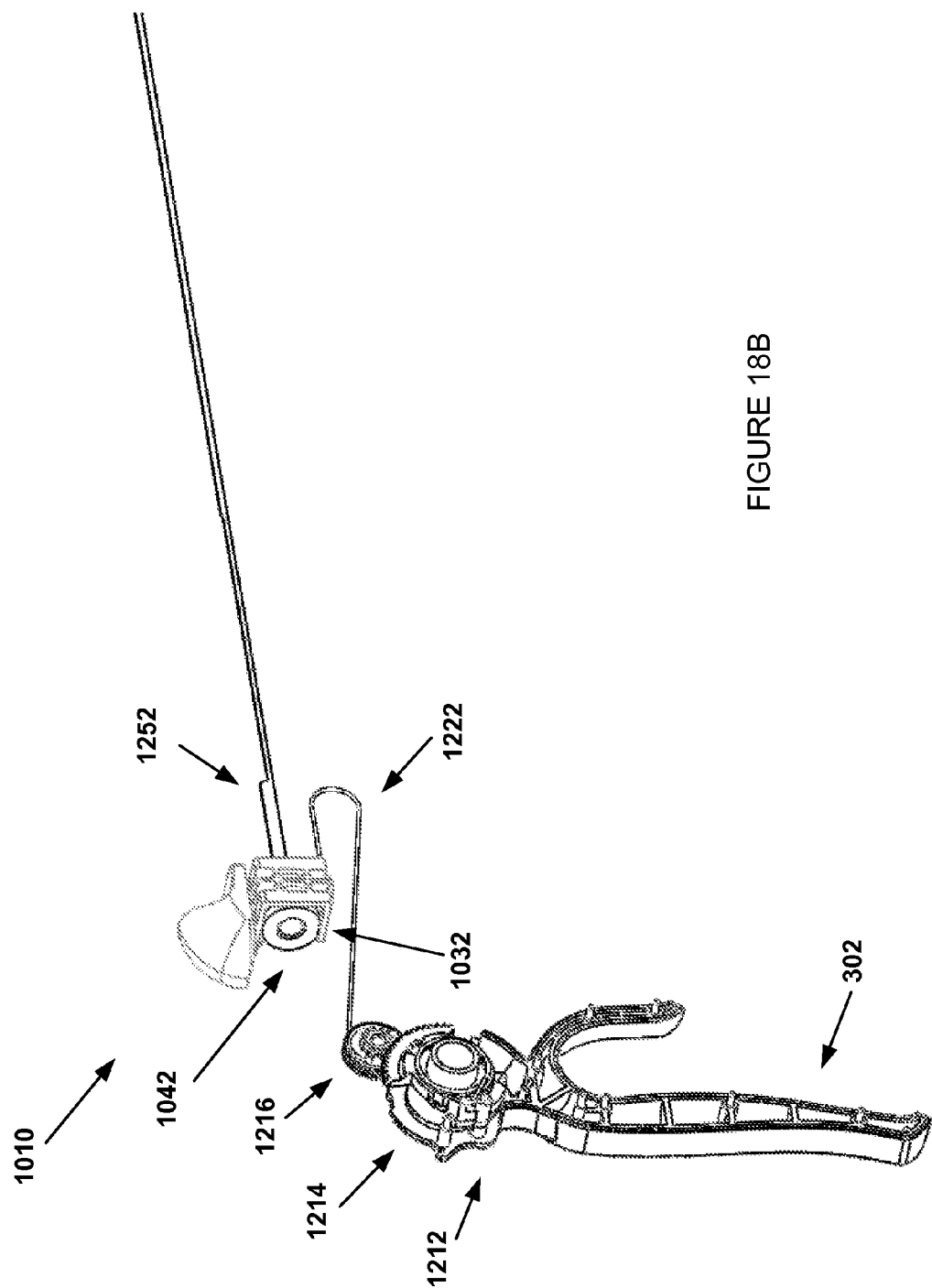

FIG. 18A and FIG. 18B illustrate the deploy mechanism components in a deployed state illustrating that components or accessories (e.g., endo-cutter or micro-cutter) attached or coupled to the deploying components have been deployed or advanced to their deployed state. For example, an endo-cutter or micro-cutter may be coupled to the deploy mechanism 1010 (such as by way of the deployment slide member 1032 and deployment spool member 1042). As the deploy mechanism components are advanced in various modes, the endo-cutter or micro-cutter is correspondingly advanced forward to cut target tissue as part of the clamping, cutting, and stapling of the endo-cutter or micro-cutter and stapling system operations.

Multiple features, aspects, and embodiments of the invention have been disclosed and described herein. Many combinations and permutations of the disclosed system may be useful in minimally invasive surgical procedures, and system may be configured to support various endo-cutters and/or stapling systems. One of ordinary skill in the art having the benefit of this disclosure would appreciate that the foregoing illustrated and describe features, aspects, and embodiments of the invention may be modified or altered, and it should be understood that the invention generally, as well as the specific features, aspects, and embodiments described herein, are not limited to the particular forms or methods disclosed, but also cover all modifications, equivalents and alternatives. Further, the various features and aspects of the illustrated embodiments may be incorporated into other embodiments, even if not so described herein, as will be apparent to those ordinary skilled in the art having the benefit of this disclosure. Although particular features, aspects, and embodiments of the present invention have been shown and described, it should be understood that the above discussion is not intended to limit the present invention to these features, aspects, and embodiments. It will be obvious to those skilled in the art that various changes and modifications may be made without departing from the spirit and scope of the present invention. Thus, the present invention is intended to cover alternatives, modifications, and equivalents that may fall within the spirit and scope of the following claims and their equivalents.

What is claimed is:

1. A surgical stapling apparatus, comprising:
    an end effector comprising
        a staple holder,
        a plurality of staples held within the staple holder, and
        an anvil pivotally connected to the staple holder;
    at least one clamp gear;
    a clamp mechanism coupled to the at least one clamp gear and to the end effector;
    at least one deployment gear;
    a deployment mechanism coupled to the at least one deployment gear and to the end effector;
    a single trigger operable to clamp the end effector and also to deploy staples therefrom; and
    a mode switch mechanism coupled to the single trigger;
    wherein the mode switch mechanism is selectively engageable with one of the clamp gear and the deployment gear, such that when the mode switch mechanism engages the clamp gear, actuation of the single trigger clamps the end effector, and when the mode switch mechanism engages the deployment gear, actuation of the single trigger deploys the staples from the end effector.

2. The surgical stapling apparatus of claim 1, wherein at least part of the clamp mechanism moves independently from at least part of the deployment mechanism.

3. The surgical stapling apparatus of claim 1, further comprising:
    a clamp lock coupled to the clamp mechanism to lock the end effector the anvil and the staple holder into a selected position.

4. The surgical stapling apparatus of claim 3, further a clamp lock release selectively disengageable comprising: from the clamp lock to release the clamp lock.

5. A method of treating tissue, comprising:
    possessing a surgical stapling apparatus comprising
        an end effector comprising
            a staple holder,
            a plurality of staples held within the staple holder, and
            an anvil pivotally connected to the staple holder;
        at least one clamp gear;
        a clamp mechanism coupled to the at least one clamp gear and to the end effector;
        at least one deployment gear;
        a deployment mechanism coupled to the at least one deployment gear and to the end effector;
        a single trigger operable to clamp the end effector and also to deploy staples therefrom; and
        a mode switch mechanism coupled to the single trigger;
        wherein the mode switch mechanism is selectively engageable with one of the clamp gear and the deployment gear;
    engaging the mode switch mechanism with the clamp gear;
    actuating the single trigger to clamp the end effector;
    engaging the mode selection switch with the deployment gear; and
    actuating the single trigger; and
    as a result of the actuating, deploying staples from the end effector.

6. The method of claim 5, wherein the deploying includes deploying staples into tissue along one of a first and a second distance.

7. The method of claim 5, further comprising, as a result of the actuating the single trigger after the engaging the mode selection switch with the deployment gear,
    cutting tissue with the end effector along one of a first and a second distance.

8. The surgical stapling apparatus of claim 1, wherein said mode switch mechanism further comprises
    a stand-off member; and
    a mode switch button selectably engageable with the stand-off member;
    wherein the stand-off member selectively engages one of the clamp gear and the deployment gear.

9. The surgical stapling apparatus of claim 3, wherein the selected position is a trocar mode.

10. The surgical stapling apparatus of claim 3, wherein the selected position is an open mode.

11. The surgical stapling apparatus of claim 3, wherein the selected position is a clamping mode.

* * * * *